United States Patent
Ahmed et al.

(10) Patent No.: US 11,376,332 B2
(45) Date of Patent: Jul. 5, 2022

(54) PLATFORM FOR ENHANCED TARGETED DELIVERY

(71) Applicant: Baylor College of Medicine, Houston, TX (US)

(72) Inventors: Nabil M. Ahmed, Houston, TX (US); Hebatalla S. Samaha, Houston, TX (US); Antonella Pignata, Houston, TX (US); Kristen Fousek, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 487 days.

(21) Appl. No.: 16/341,412

(22) PCT Filed: Apr. 7, 2017

(86) PCT No.: PCT/US2017/026535
§ 371 (c)(1),
(2) Date: Apr. 11, 2019

(87) PCT Pub. No.: WO2018/071058
PCT Pub. Date: Apr. 19, 2018

(65) Prior Publication Data
US 2019/0240343 A1  Aug. 8, 2019

Related U.S. Application Data

(60) Provisional application No. 62/408,753, filed on Oct. 15, 2016.

(51) Int. Cl.
| | | |
|---|---|---|
| *A61K 47/64* | (2017.01) | |
| *C07K 14/705* | (2006.01) | |
| *A61K 39/38* | (2006.01) | |
| *A61K 39/39* | (2006.01) | |
| *A61K 48/00* | (2006.01) | |
| *A61P 31/10* | (2006.01) | |
| *A61P 5/00* | (2006.01) | |
| *A61P 35/00* | (2006.01) | |
| *A61K 35/17* | (2015.01) | |
| *A61K 35/28* | (2015.01) | |

(52) U.S. Cl.
CPC .......... *A61K 47/6425* (2017.08); *A61K 35/17* (2013.01); *A61K 35/28* (2013.01); *A61K 39/38* (2013.01); *A61K 39/39* (2013.01); *A61K 48/00* (2013.01); *A61P 5/00* (2018.01); *A61P 31/10* (2018.01); *A61P 35/00* (2018.01); *C07K 14/70596* (2013.01); *C07K 2319/02* (2013.01); *C07K 2319/03* (2013.01); *C07K 2319/33* (2013.01); *C07K 2319/70* (2013.01)

(58) Field of Classification Search
CPC ................................................. A61K 47/6425
See application file for complete search history.

(56) References Cited

U.S. PATENT DOCUMENTS

| | | | | |
|---|---|---|---|---|
| 2002/0041874 A1* | 4/2002 | Mundy | .............. | C07K 16/2836 |
| | | | | 424/131.1 |
| 2015/0111814 A1* | 4/2015 | Abrams | ............... | C07K 14/195 |
| | | | | 514/3.8 |

OTHER PUBLICATIONS

Greineder et al. (PLoS ONE 2013; 8(11): e80110) (Year: 2013).*
Greineder et al. ((2013) "Vascular Immunotargeting to Endothelial Determinant ICAM-1 Enables Optimal Partnering of Recombinant scFv-Thrombomodulin Fusion with ndogenous Cofactor." PLoS ONE 8(11): e80110. doi:10.1371/journal.pone.0080110). (Year: 2013).*
Oliveira et al. "CD6 attenuates early and late signaling events, setting thresholds for T-cell activation", Eur J Immunol. 2012, 42(1): 195-205; Abstract, p. 196, col. 2; p. 198, col. 2; p. 202, col. 1.
Chappell et al. "Structures of CD6 and Its Ligand CD166 Give Insight into Their Interaction", Structure 2015, 23 (8):1426-36; Abstract, p. 1427, Fig 1 and its legend; p. 1429, Figure 2, and its legend; p. 1432, col. 2.
Federman et al. "Enhanced growth inhibition of osteosarcoma by cytotoxic polymerized liposomal nanoparticles targeting the alcam cell surface receptor", Sarcoma. 2012, 2012:126906; Abstract, p. 9, Table 1; p. 10, col. 1.

* cited by examiner

*Primary Examiner* — Scott Long
(74) *Attorney, Agent, or Firm* — Norton Rose Fulbright US LLP

(57) ABSTRACT

Embodiments of the disclosure concern methods and compositions for delivering therapeutic, diagnostic or interventional moieties, such as complex and simple entities such as biologies, including at least cells, for example. The methods employ targeted delivery by employing at least one ALCAM-binding moiety on the therapeutic, diagnostic or interventional moiety to be delivered. In specific cases, the ALCAM-binding moiety is present on or with the therapeutic moiety in multiple iterations. In certain embodiments, the ALCAM-binding moiety comprises at least one SRCR domain from CD6 and a stalk, such as from CD6, of the secretable or molecular form thereof.

27 Claims, 36 Drawing Sheets

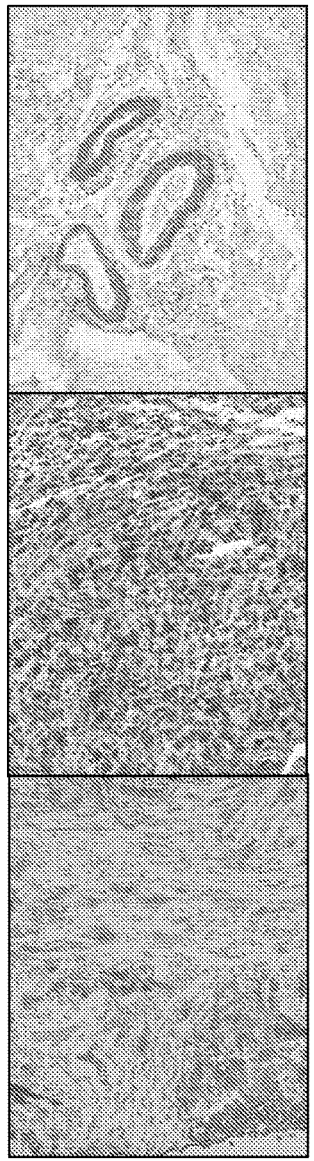
FIG. 1A ALCAM is upregulated in Brain Tumor (Vascular and Perivascular region)
1st donor  2nd donor  3rd donor
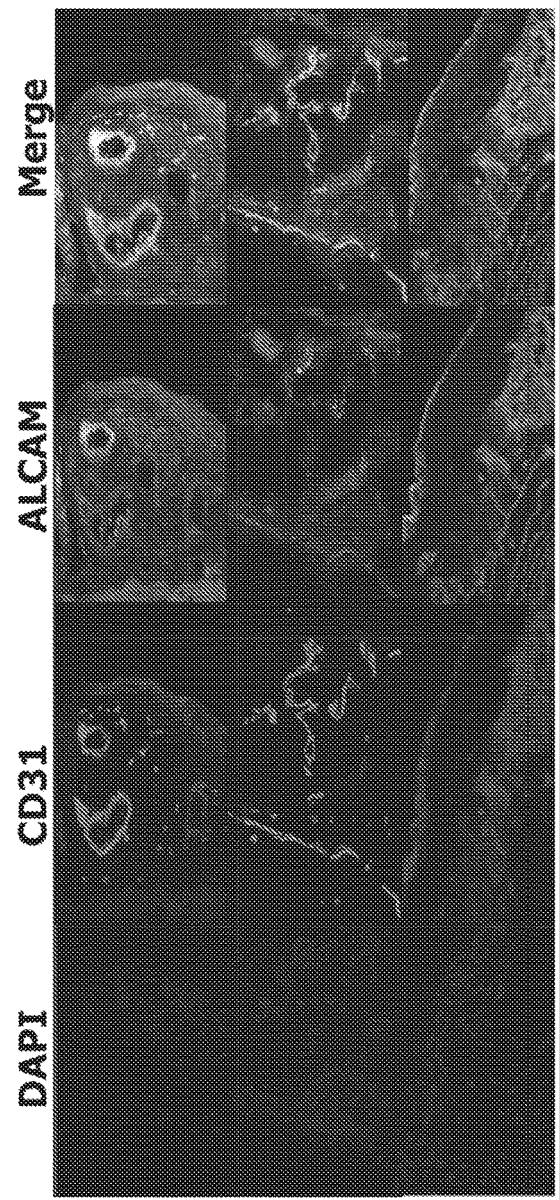
FIG. 1B DAPI  CD31  ALCAM  Merge

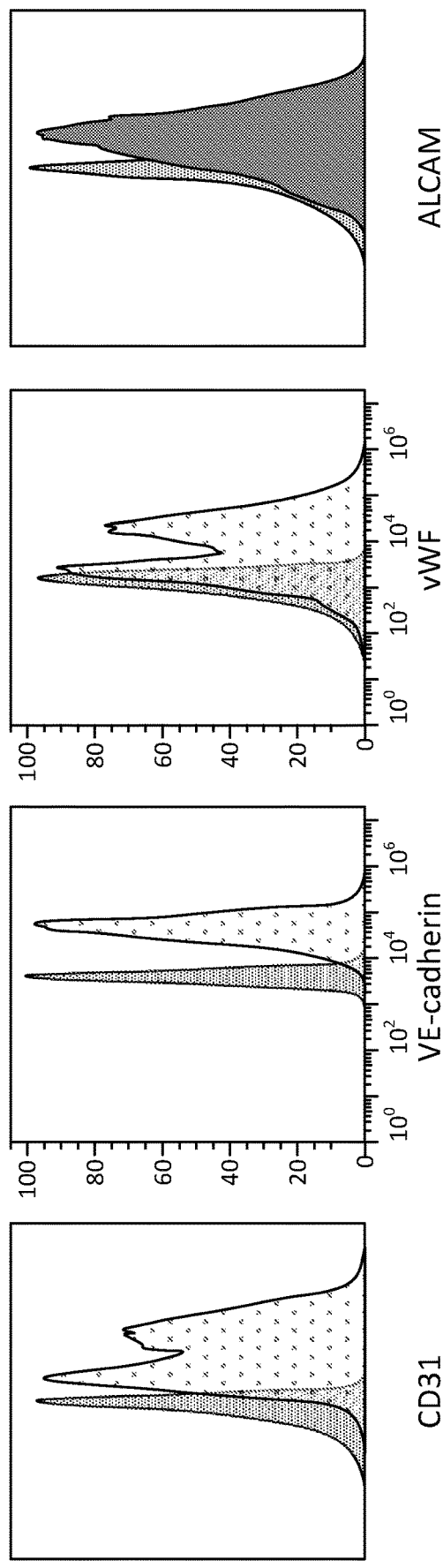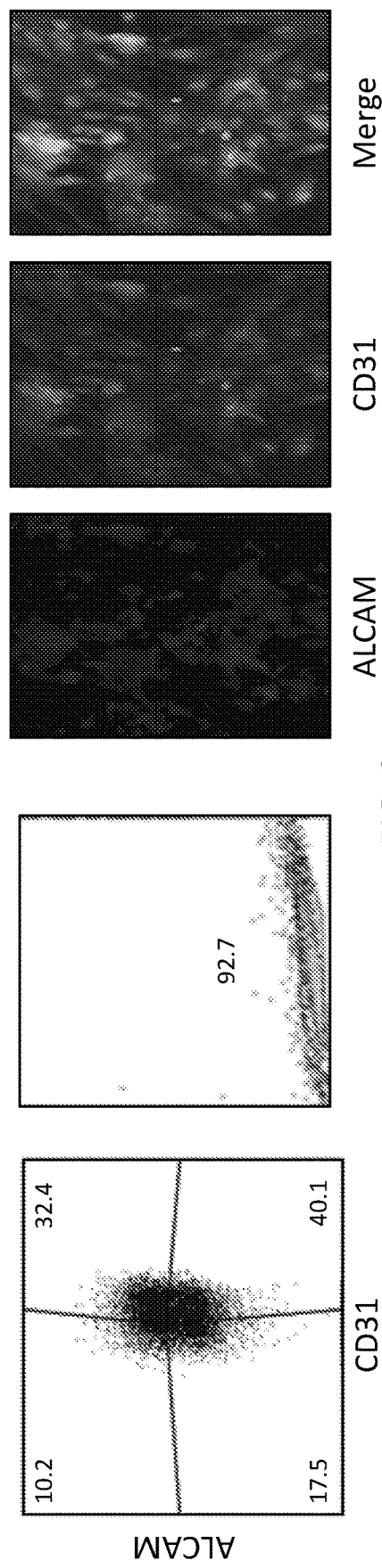
FIG. 2

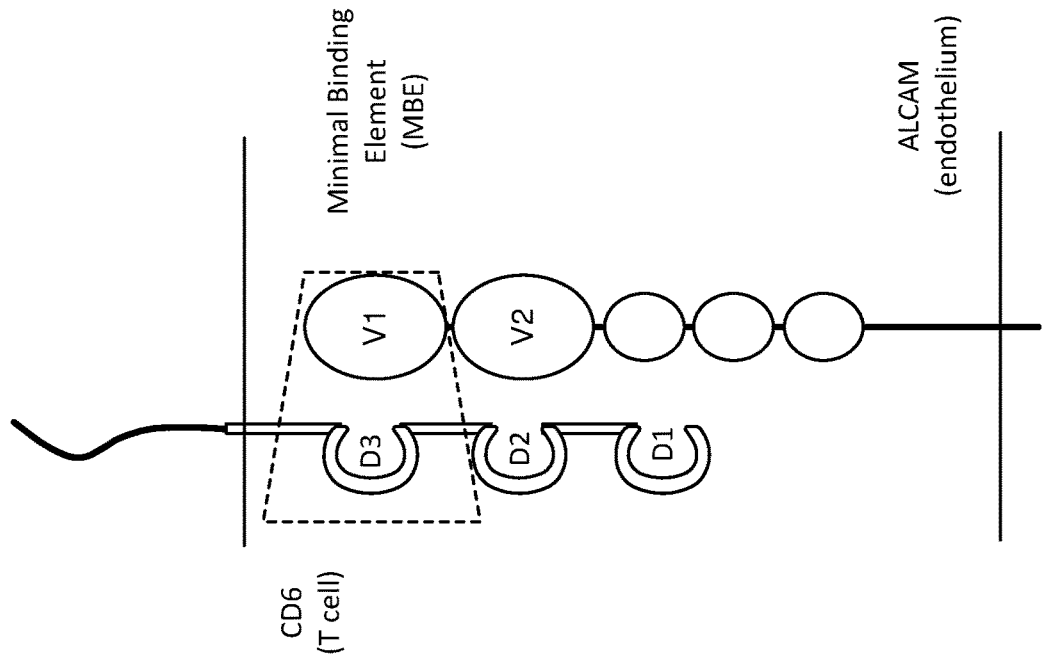

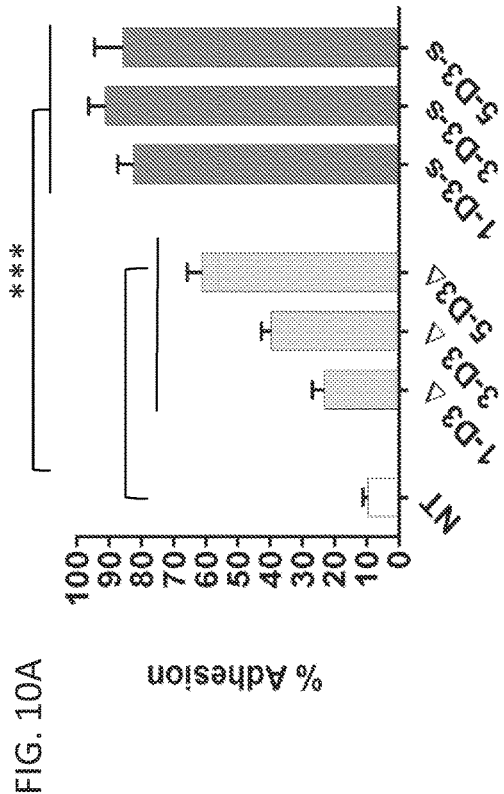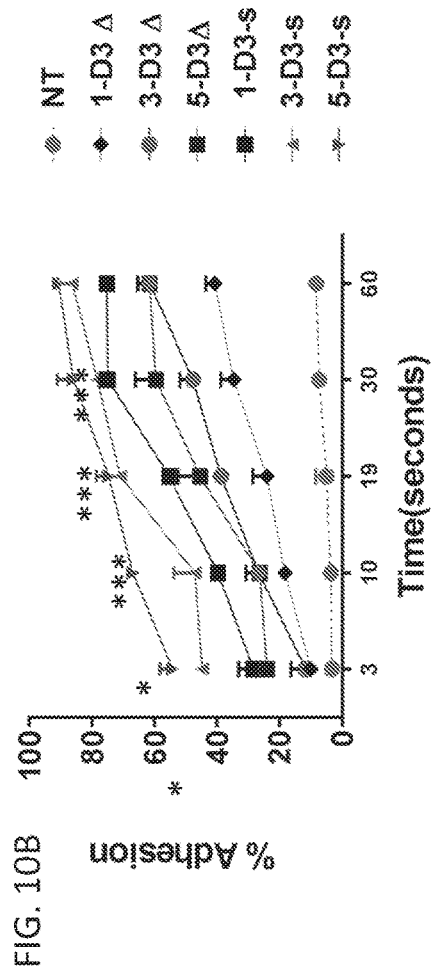
FIG. 10A
FIG. 10B

Molecule 1: CD6 MBE Monomer Truncated

AGTAGACGGCATCGCAGCTTGGATACACGCCCCA
CGTGAAGGCTGCCGACCCCGGGGGTTGACCATCCTC
TAGACTGCCATGTGGCTCTTCGGGATCACTGGAT
TGCTGACGGCAGCCCTCAGGTGGCCTGACAG
GGGGCGCTGACCGCTGCGAGGGCAGGTGGAGGTA
CACTTCCGAGGGTCTGAACACAGTGTGACAGT
GAGTGGTACCCATCGGAGGCCAAGGTGCTCTGCCAG
TCCTTGGGCTGTGGAAC

Molecule 2: CD6 MBE Monomer with Signaling Domain

AGTAGACGGGCATCGCAGCTTGGATACACGCGCCGCCCACGTGAAGGCTGCGACCCCGG
GGGTTGACCATCCTCTAGACTGCCATGTGGCTCTCTTCGGATCACTGGATTGCTGA
CGGCAGCCCTCTCAGGTTGGCGCCTGACAGGGGCGCTGACCGCTGCGAGGGCAGG
TGGAGGTACACTTCCGAGGGTCTGAACACAGTGTGTGACAGTGAGTGTACCCAT
CGGAGGCCAAGGTGCTCTGCCAGTCCTTGGGCTGTGAACTGCGGTTGAGAGGCCCA
AGGGGCTGCCCCACTCCTTGTCCGCAGGATGTACTACTCATGCAATGGGAGGAGC
TCACCCTCTCCAACTGCTCCTGGCGGTTCAACAACTCCAACCTCTGCAGCCAGTCGCT
GGCAGCCAGGGTCCTCTGCTCAGCTTCCCGGAGTTGCACAATCTGTCCACTCCCGAA
GTCCCTGCAAGTGTTCAGACAGTCACTATAGAATCTTCTGTGACAGTGAAAATAGAG
AACAAGGAATCTCGGGAGCTAATGCTCCTCATCCCCTCCATCGTTCTGGGAATTCT
CCTCCTTGGCTCCCTCATCTTCATAGCCTTCATCTCTTGAGAATTAAGGAAAATAT
GCCCTCCCCGTAATGGTGAACCACCAGCACCTACCCACCATCCCGGCAGGGAGCAAT
AGCTATCAACCGGTCCCCATCACCATCCCCAAAGAAGTTTTCATGCTGCCCATCCAGGTCC
AGGCCCCGCCCCTGAGGACTCAGACTCTGGCTCGGACTCAGACTATGAGCACTATGACT
TCAGCGCCCAGCCTCCTGTGGCCCAAGCAGGTTCCAGATGCCACCCTTGGAGGCCATCGGGTCA
CAGATGAGGAGGTCAGCAAAGCAGGTTCCAGATGCCACCCTTGGAGGAAGGACTTGAAG
AGTTGCATGCCCTCCCCACATCCCAACTGCCAACCTGGACACTGCATTACAGACCCGCCATC
CCTGGGCCCCTCAGTATCACCCGAGGAGCAACAGTGAGTGAGCACCTCTTCAGGGGAGGA
TTACTGCAATAGTCCCAAAGCAAGCTGCCTCCATGAACCCCCAGGTGTTTCTTCAGAGA
GGAGTTCCTTCCTGGAGCAGCCCCAAACTTGGAGCTGGCCGGCACCAGCCAGCCTTT
CAGCAGGGCCCCCGGCTGATGACAGCTCCAGCACCTCATCCGGGGAGTGGTACCAGAACT
TCCAGCCACCACCCCAGCCCGGCTGCCGACAACGATGACTACGATGACATCAGCGACGCCAGCC
CTCAGCCTGACTCCACCGACCGACAACGATGACTACGATGACATCAGCGGACGCCAGCGGAGCTAAT
TATAACAGCCAGCTCGAACGCGTCACCACCGA

FIG. 22

Molecule 3: CD6 MBE Trimer Truncated

AGTAGACGGCATCGCAGCTTGGATACACGCCGCCCACGTGAAGGCTGCCGACCCCGGGGGTTGACCATCC
TCTAGACTGCCATGTGGCTCTTCTTCGGGATCACTGGATTGCTGACGGCAGCCCTCTCAGGTTGGCGCCTG
ACAGGGGGCGCTGACCGCTGCGAGGGGCAGGTGGAGGTACACTTCCGAGGGGTCTGGAACACAGTGTGTG
ACAGTGAGTGGTACCCATCGGAGGCCAAGGTGCTCTGCCAGTCCTTGGGCTGTGGAACTGCGGTTGAGAG
GCCCAAGGGGCTGCCCCACTCCTTGTCCGGCAGGATGTACTACTCATGCAATGGGGAGGAGCTCACCCTCT
CCAACTGCTCCTGGCGGTTCAACAACTCCAACCTCTGCAGCCAGTCGCTGGCAGCCAGGGTCCTCTGCTCA
GCTTCCCGGAGTTTGCACAATCTGTCCACTCCCGAAGTCCCTGCAAGTGTTCAGACAGTCACTATAGAATC
TTCTGTGACAGTGAAAATAGAGAACAAGGAATCTCGGGAGCTAATGCTCCTCTGGCGCCTGACAGGGGGC
GCTGACCGCTGCGAGGGGCAGGTGGAGGTACACTTCCGAGGGGTCTGGAACACAGTGTGTGACAGTGAGT
GGTACCCATCGGAGGCCAAGGTGCTCTGCCAGTCCTTGGGCTGTGGAACTGCGGTTGAGAGGCCCAAGGG
GCTGCCCCACTCCTTGTCCGGCAGGATGTACTACTCATGCAATGGGGAGGAGCTCACCCTCTCCAACTGCT
CCTGGCGGTTCAACAACTCCAACCTCTGCAGCCAGTCGCTGGCAGCCAGGGTCCTCTGCTCAGCTTCCCGG
AGTTTGCACAATCTGTCCACTCCCGAAGTCCCTGCAAGTGTTCAGACAGTCACTATAGAATCTTCTGTGAC
AGTGAAAATAGAGAACAAGGAATCTCGGGAGCTAATGCTCCTCTGGCGCCTGACAGGGGGCGCTGACCGC
TGCGAGGGGCAGGTGGAGGTACACTTCCGAGGGGTCTGGAACACAGTGTGTGACAGTGAGTGGTACCCAT
CGGAGGCCAAGGTGCTCTGCCAGTCCTTGGGCTGTGGAACTGCGGTTGAGAGGCCCAAGGGGCTGCCCCA
CTCCTTGTCCGGCAGGATGTACTACTCATGCAATGGGGAGGAGCTCACCCTCTCCAACTGCTCCTGGCGGT
TCAACAACTCCAACCTCTGCAGCCAGTCGCTGGCAGCCAGGGTCCTCTGCTCAGCTTCCCGGAGTTTGCAC
AATCTGTCCACTCCCGAAGTCCCTGCAAGTGTTCAGACAGTCACTATAGAATCTTCTGTGACAGTGAAAAT
AGAGAACAAGGAATCTCGGGAGCTAATGCTCCTCATCCCCTCCATCGTTCTGGGAATTCTCCTCCTTGG
CTCCCTCATCTTCATAGCCTTCATCCTCGGGAGCTAATTATAACAGCCAGCTCGAACGCGTCACCACCG
A

FIG. 23

Molecule 4: CD6 MBE Trimer with Signaling

```
AGTAGACGGCATCGCAGCTTGGATACACGCCGCCCACGTGAAGGCTGCCGACCCGGGGGTTGACCATCTCTAGACTGCC
ATGTGGCTCTTCTCGGATCACTGGATTGCTGACGGCAGCCCTCAGGTTGGCGCTGACAGGGGCGCTGACCGCTGCG
AGGGGCAGGTGGAGGTACACTTCCGAGGGTCTGGAACACAGTGTGACAGTGAGTGGTACCCATCGGAGGCCAAGGTG
CTCTGCCAGTCCTTGGGCTGTGTGAAGGAGCTCACCCTCTCCAACTGCGGTTCAACAACTCTGCACTCCTTGTCCGCAGGATGTACTACT
CATGCAATGGGGAGGAGTCACTCTGCTCAGTTCCCTCTGGTTGCACATCGTCCCGAAGTGTTCAGACAGTCACTATA
CAGGGTCCTCTGCTCAGTTCCCTCTGGAGTTTGCACAATCGTCCCGAAGTGTCTGCAAGTGTTCAGACAGTCACTATA
GAATCTTCTGTGACAGTGAAATAGAGAACAAGGAATCTCGGAGTAATGCTCCTGGCGCCTGACAGGGGCGCTGAC
CGCTGCGAGGGGCAGGTGGAGGTACACTTCCGAGGGTCTGGAACACAGTGTGACAGTGAGTGGTACCCATCGGAGGC
CAAGGTGCTCTGCCAGTCCTTGGGCTGTGTGAAGGGTCCCCACTCCTTGTCCGGCAGGAT
GTACTACTCATGCAATGGGGAGGAGTCACCCTCTCCAACTCTGCTCAACAACTCCAACTCTGCAGCCAGTCG
CTGGCAGCCAGGGTCCTCTGCTCAGTTCCCGGAGTTTGCACAATCGTCCCACTCCTGCAAGTGTTCAGACAG
TCACTATAGAATCTTCTGTGACAGTGAAATAGAGAACAAGGAATCTCGGGAGCTAATGCTCCTCTCATCCCCTCC
GCGCTGACCGCTGCGAGGGGCAGGTGGAGGTACACTTCCGAGAACAGTGTGACAGTGAGTGGTACCCAT
CGGAGGCCAAGGTGCTCTGCCAGTCGTGCCCACTCCTTGTCCG
GCAGGATGTACTACTCATGCAATGGGGAGGAGCTCAGTCTCCAACTGCTCTGGCGGTTCAACAACTCCAACTCTGCAG
CCAGTCGCTGCGCAGCCAGGGTCCTCTGCTCAGTTCCCGGAGTTTGCACAATCTGTCCACTCCGAAGTCCCTGCAAGTGTT
CAGACAGTCACTATAGAATCTTCTGTGACAGTGAAATAGAGAACAAGGAATCTCGGGAGCTAATGCTCCTCTCATCCCCTCC
ATCGTTCTGGGAATTCTCCCTCCTTGGCTCCCTCATAGCCTTCATCCTCTTGAGAATTAAAGGAAATATGCCCTCC
CCGTAATGGTGAACCACCAGCACCTACCCAGGTCCAGCCCCGCCCCAGCAGAATAGTATCAACCGGTCCCATCACCATCCCCAA
GAAGTTTTCATGCTGCCCAGCCTCCTGTGGCCCTGACCCACCTTCTACAATTCCCAGGCGCATCGGGTCACAGATGAGGAGTCCAGCA
CTTCAGCGCCCAGCCCTCCTGTGGCCCTGACCACCTTCTACAATTCCCAGGCGCATCGGGTCACAGATGAGGAGTCCAGCA
GGTTCCAGATGCCACCCCTTGGAGGAAGGACTTGAAGAGTTGCATGCCTCCCACATCGCCAACCCTGCCGACACTGCATTACA
GACCCGGCCATCCCTGGCCCTCAGTATCACCGAGGAGCAACAGTGAGTGAGCACCCTCTCAGGGAGGATTACTGCAATAGTCC
CAAAAGCAAGCTGCCTCCATGGAACCCCCCCAGTGTTTCTTCAGAGAGGAGTTCCTTCCTGGAGCAGCCCCCAAACTTGGAGCTGG
CCGGCACCCAGCCCAGCCTTTCAGCAGGGCCCCCGGCTGATGACAGCTCCAGGCACCTCATCCGGGAGTGGTACCAGAACTTCCA
GCCACCACCCCAGCCCCCCAGCCCCCCCTTCGGAGGAGCAGTTGGCTGTCCAGGTCCCCCAGCCCCTGACTCGACTCCACCGACCGATGAC
TACGATGACATCAGCGACGGCGGAGCCGGGGAGCTAATTATAACAGCCAGCTCGAACGCGGTCACCACCGA
```

FIG. 24

Molecule 5: CD6 Pentamer Truncated

AGTAGACGGCATCGCAGCTTGGATACACGCCGCCCACGTGAAGGCTGCCGACCCCGGGGGTTGACCATCCTCTAGACTGCCATGTGG
CTCTTCTTCGGGATCACTGGATTGCTGACGGCAGCCCTCTCAGGTTGGCGCCTGACAGGGGGCGCTGACCGCTGCGAGGGGCAGGTG
GAGGTACACTTCCGAGGGGTCTGGAACACAGTGTGTGACAGTGAGTGGTACCCATCGGAGGCCAAGGTGCTCTGCCAGTCCTTGGGC
TGTGGAACTGCGGTTGAGAGGCCCAAGGGGCTGCCCCACTCCTTGTCCGGCAGGATGTACTACTCATGCAATGGGGAGGAGCTCACC
CTCTCCAACTGCTCCTGGCGGTTCAACAACTCCAACCTCTGCAGCCAGTCGCTGGCAGCCAGGGTCCTCTGCTCAGCTTCCCGGAGTT
TGCACAATCTGTCCACTCCCGAAGTCCCTGCAAGTGTTCAGACAGTCACTATAGAATCTTCTGTGACAGTGAAAATAGAGAACAAGG
AATCTCGGGAGCTAATGCTCCTCTGGCGCCTGACAGGGGGCGCTGACCGCTGCGAGGGGCAGGTGGAGGTACACTTCCGAGGGGTCT
GGAACACAGTGTGTGACAGTGAGTGGTACCCATCGGAGGCCAAGGTGCTCTGCCAGTCCTTGGGCTGTGGAACTGCGGTTGAGAGGC
CCAAGGGGCTGCCCCACTCCTTGTCCGGCAGGATGTACTACTCATGCAATGGGGAGGAGCTCACCCTCTCCAACTGCTCCTGGCGGTT
CAACAACTCCAACCTCTGCAGCCAGTCGCTGGCAGCCAGGGTCCTCTGCTCAGCTTCCCGGAGTTTGCACAATCTGTCCACTCCCGAA
GTCCCTGCAAGTGTTCAGACAGTCACTATAGAATCTTCTGTGACAGTGAAAATAGAGAACAAGGAATCTCGGGAGCTAATGCTCCTC
TGGCGCCTGACAGGGGGCGCTGACCGCTGCGAGGGGCAGGTGGAGGTACACTTCCGAGGGGTCTGGAACACAGTGTGTGACAGTGA
GTGGTACCCATCGGAGGCCAAGGTGCTCTGCCAGTCCTTGGGCTGTGGAACTGCGGTTGAGAGGCCCAAGGGGCTGCCCCACTCCTT
GTCCGGCAGGATGTACTACTCATGCAATGGGGAGGAGCTCACCCTCTCCAACTGCTCCTGGCGGTTCAACAACTCCAACCTCTGCAGC
CAGTCGCTGGCAGCCAGGGTCCTCTGCTCAGCTTCCCGGAGTTTGCACAATCTGTCCACTCCCGAAGTCCCTGCAAGTGTTCAGACAG
TCACTATAGAATCTTCTGTGACAGTGAAAATAGAGAACAAGGAATCTCGGGAGCTAATGCTCCTCTGGCGCCTGACAGGGGGCGCTG
ACCGCTGCGAGGGGCAGGTGGAGGTACACTTCCGAGGGGTCTGGAACACAGTGTGTGACAGTGAGTGGTACCCATCGGAGGCCAAG
GTGCTCTGCCAGTCCTTGGGCTGTGGAACTGCGGTTGAGAGGCCCAAGGGGCTGCCCCACTCCTTGTCCGGCAGGATGTACTACTCAT
GCAATGGGGAGGAGCTCACCCTCTCCAACTGCTCCTGGCGGTTCAACAACTCCAACCTCTGCAGCCAGTCGCTGGCAGCCAGGGTCC
TCTGCTCAGCTTCCCGGAGTTTGCACAATCTGTCCACTCCCGAAGTCCCTGCAAGTGTTCAGACAGTCACTATAGAATCTTCTGTGAC
AGTGAAAATAGAGAACAAGGAATCTCGGGAGCTAATGCTCCTCTGGCGCCTGACAGGGGGCGCTGACCGCTGCGAGGGGCAGGTGG
AGGTACACTTCCGAGGGGTCTGGAACACAGTGTGTGACAGTGAGTGGTACCCATCGGAGGCCAAGGTGCTCTGCCAGTCCTTGGGCT
GTGGAACTGCGGTTGAGAGGCCCAAGGGGCTGCCCCACTCCTTGTCCGGCAGGATGTACTACTCATGCAATGGGGAGGAGCTCACCC
TCTCCAACTGCTCCTGGCGGTTCAACAACTCCAACCTCTGCAGCCAGTCGCTGGCAGCCAGGGTCCTCTGCTCAGCTTCCCGGAGTTT
GCACAATCTGTCCACTCCCGAAGTCCCTGCAAGTGTTCAGACAGTCACTATAGAATCTTCTGTGACAGTGAAAATAGAGAACAAGGA
ATCTCGGGAGCTAATGCTCCTCATCCCCTCCATCGTTCTGGGAATTCTCCTCCTTGGCTCCCTCATCTTCATAGCCTTCATCCTC
GGGAGCTAATTATAACAGCCAGCTCGAACGCGTCACCACCGA

FIG. 25

Molecule 6: CD6 MBE Pentamer + Signaling

```
AGTAGACGGCATCGACGCTTGGATACACGCGCCCACGTGAAGGCTGCGACCCGGGGTTGACCATCCTCTAGACTGCCATGTGGCTCT
TCTTCGGGATCACTGGATTGCTGACGCGCAGCCCTCTCAGGTTGGCGCTGACGGTGCTGCGCCTGACCGCTGCGAGGGGCAGGTGGAGGTAC
ACTTCCGAGGGTCTGAACACAGTGTGACAGTGAGTGGTACCCATGGAGGCAAGGTGCTCTGCCAGTCCTTGGCTGTGGAACTGC
GGTTGAGAGGCCAAGGGGCTGCCCACTCCTTGTCCGGCAGGATGTACTACTGCAATGGGAGGAGCTCACCCTCTCAACTGCTCC
TGGCGGTTCAACAACTCCAAGTGTTCAGACAGTCACTATAGAATCTCTGTGACAGGTCCTCAGTCCCGAGTTGCACAATCTGTCCACTCC
CGAAGTCCCTGCAGAGGGGCGCTGACAGTGTCTGCCAGTCCTTGGCTGTGGAGGTACACTTCGTTGAACACAAGGAATCTCGGGAGCTAATGCTCTC
TGGCGCCTGACAGGGGGGCGCTGACCGGTGCTCTGCCAGTGCTTGGCTGTGGAACTGCGTTGAGAGGCCAAGGGTGTGACAGTGAGTGG
TACCCATCGGAGGCCAAGGGTGCTCTGCCAGTGCTTGGCTGTGGAACTGCGTTGAGAGGCCAAGGGTGCCCAACTCTGCAGCCAGTCCGGCA
GGATGTACTACTGCAATGGGAGGAGCTCACCCTCTCAACTGCTCCAACAACTCCAAGTGTTCAGACAGTCACTATAGAATCTT
AGCCAGGTCCCTGCTCAGTTCCCGGAGTTGCACAATCTGTCCACTCCCGAAGTGTTCAGACAGTCACTATAGAATCTCTGGAGTGGTCCTGCCAGGA
CTGTGACAGTGAAAATAGAGAACAAGGAATCTCGGAGGGTCTGAACACAGTGCCCCACTCCTGGCCTGACAGTCCTGTGCCCAGTCCTGGGCTG
TGGAGGTACACTTCCGAGGGTCTGAACTGGCGGTTGGCGCCCAAGTCCTGCCAGTGCTCCTGGGAGGAGCTCAACCCTCTCC
TGAACTGCGGTTGAGAGGCCAAGGGGCTGCCCATGCAATGGGAGGAGCTCACCCTCTCAACTGCTCCAACAACTCCAAGTGCTGTGGCGGG
AACTGCTCCTGGCGGTTCAACAACTCCAAGTCCCTGCAGTCCCTGCAGACAGTGCCCAGGTCCCTGCTCAGTTCCCGGAGTTGCACAATCT
GTCCACTCCCGAAGTCCCTGCAGAGTGTTCAGACAGTCACTATAGAATCTCTGTGACAGTGAAAATAGAGAACAAGGAATCTCGGAGCTA
ATGCTCCTTGGCGCCTGACAGGGGGTCTGAAGTGGTACACTTCGAGGGTCTGAACACAGTGTGTGAC
AGTGAGTGGTACCCATCGGAGGCCAAGGTGCTCTGCCAGTCCTTGGGGCTGTGGAACTGCGTTGAGAGGCCAAGGGCTGCCCACTCCT
GTCGGCTGGCAGCCAGGTCCCTGCTCAGTTCCCGGAGTTGCACAATCTGTCCACTCCCGAAGTGTTCAGACAGTCACTA
TAGAATCTCTGTGACAGTGAAAATAGAGAACAAGGAATCTCGGGAGCTAATGCTCCTGGCCTGACAGTGTGTCTGCCAGT
AGGGGCAGGTGGAGGTACACTTCCGAGGGTCTGAACTGGCGGTTGGCGCCCAAGTCCTGCCAGTGCTCCTGGGAGGAGCTCAGT
CCTTGGCTGTGAACTGCGGTTGAGAGGCCAAGGGGCTGCCCATGCAATGGGAGGAGCTCAGTCTATACTACTGCTCCAGT
CACCCTCTCAACTGCTCCAACAACTCCAAGTGTTCAGACAGTCACTATAGAATCTCGGGAATAGAGAACAAGGAATC
TGCACAATCTGTCCACTCCCGAAGTCCCTGCAGAGTTCCCGTAATGCGTGAACCAGCACCTACCCGCCCCCGCCCATCACC
TCGGGAGCTAATGCCCCTCCCCGTAATGCGTGAACCAGCACCTACCCGCCCCCGCCCATCACCAGGAGCAATAGCTCCCATGAGAAT
TAAAGGAAAATATGCCCCCCCGTAATGGTGAACCAGCACCTACCCGCCCCCGCCCATCAGCAGCAATAGCTATCACCGGTCCCATCACC
ATCCCCAAAGAAGTTTCATGCTGTGCCCATCCAGGTTCCAGGTTCCAGCTCCGAGGACTCAGACTCTGGCTCGGACTCAGACTATGAGCACTATGACT
TCAGCGCCCAGCCCTCCGTGCCCCTGACCACCTTCTACAATTCCAGGCGGCATCGGTCACAGATGAGGAGGTCCAGGAAAGCAGGTTCCAGATGC
CACCCCTTGGAGGAAGGACTTGAAGAGTTTGCATGCCTCCCACATCCCAACTGCCAACCCTGGACACTGCATTACAGACCCGCCATCCCTGGGCCCTC
AGTATCACCCGAGGAGCAACAGTGAGTCGAGCACCCTCTTCAGGGGAGGATTACTGCACATCCCAAAGCAAGCTGCCTCCATGGAACCCCCAGG
TGTTTTCTTCAGGAGGGTCCTTCCGGAGAGTGGTACCAGCAGCCCCAAACTTGGAGCACCACCCCCAGCCGCCCCCCCTCAGCAGGGCCAGCCCTTTCAGCAGGAGCAGTTTGGCTGTCGTCCAGGGTCCCC
ACAGCTCCACCCTCATCCGGAGAGTGGTACCAGCAGCCCAAACTTGGAGCACCACCCCCAGCCGCCCCCCCTCAGCAGGGCCAGCCCTTTCAGCAGGAGCAGTTTGGCTGTCGTCCAGGGTCCCC
AGCCCCTCAGCCTGACTCCACCGACAACGACTACGATGACTACGATGACATCAGCCGCCGGAGCTAATTATAACAGCCAGTCGAACGGCGTCACCAC
CGA
```

FIG. 26

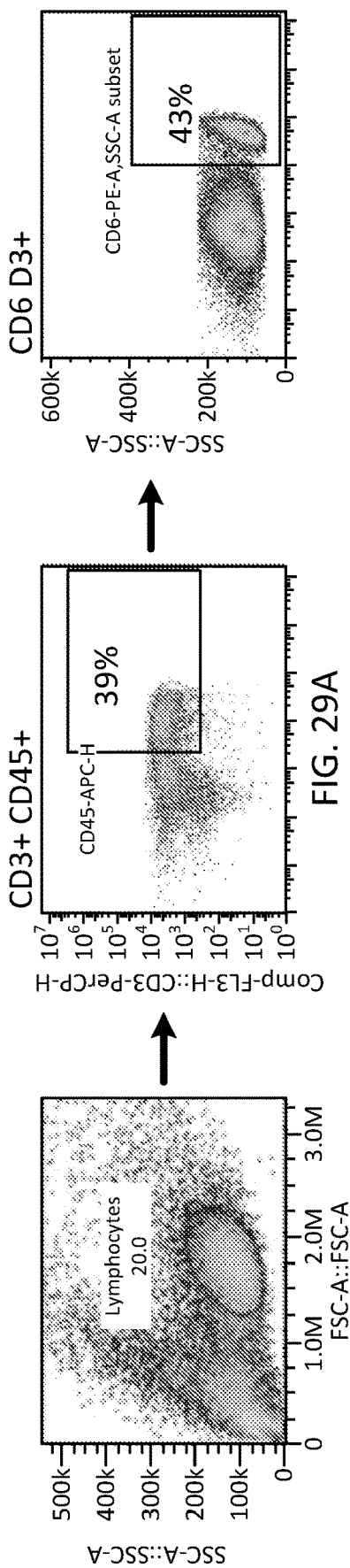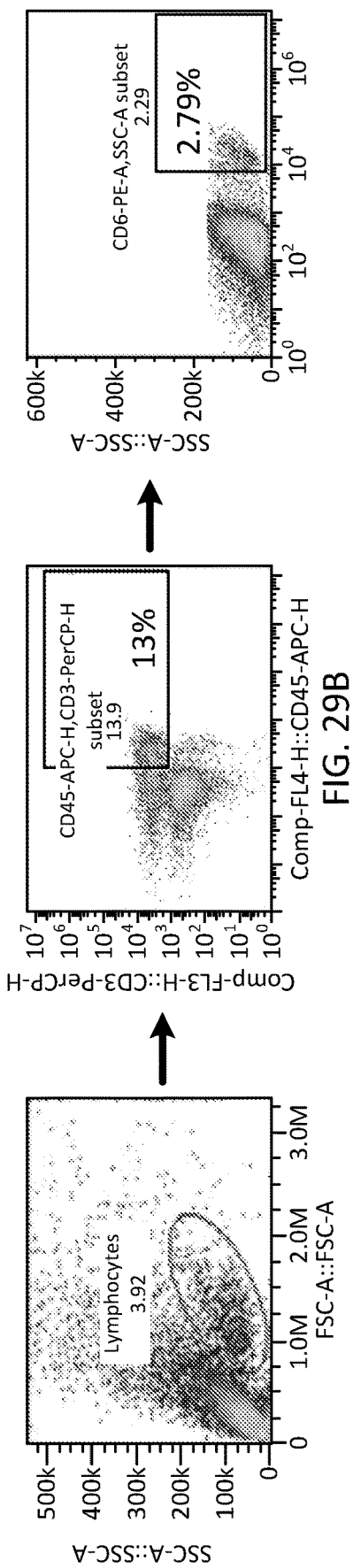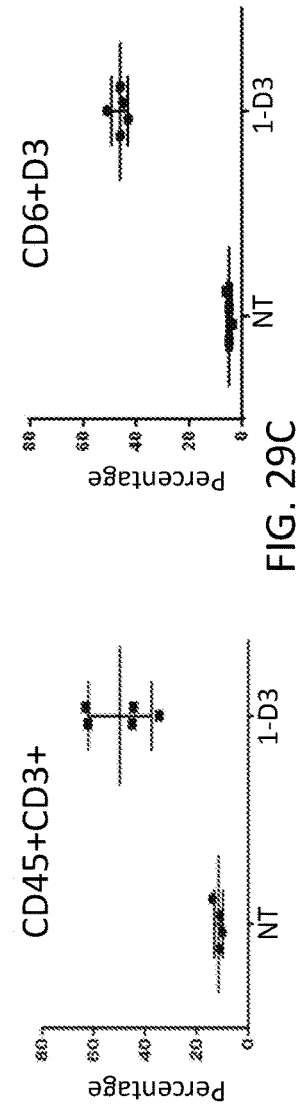
T cells home and Specifically Infiltrate GBM Explants
FIG. 29A
FIG. 29B
FIG. 29C

MBE Endodomain Induces Mechanical Stability of the Migrating T Cells

Stretch-induced FAK redistribution after D3-AlCAM interaction in MBE T Cells

PLATFORM FOR ENHANCED TARGETED DELIVERY

This application is a national phase application under 35 U.S.C. § 371 that claims priority to International Application No. PCT/US2017/026535 filed Apr. 7, 2017, which claims priority to U.S. Provisional Patent Application No. 62/408, 753, filed Oct. 15, 2016, which is incorporated by reference herein in its entirety.

TECHNICAL FIELD

Embodiments of the disclosure concern at least the fields of cell biology, molecular biology, immunology, therapeutics, imaging, and medicine.

BACKGROUND

A successful homing of immune and other cells to their destination entails breaching efficiently the endothelial/epithelial barrier. Interaction of immune and other cell surface receptor with their cognate adhesion molecules over endothelium is a kick-start for cellular extravasation. The latter process is a multistep cascade, which involves cell capture, arrest, rolling, and tethering, firm adhesion and eventually transendothelial migration (TEM).

ALCAM (CD166), an adhesion molecule belonging to the immunoglobulin superfamily, has recently been reported to be involved leukocyte through endothelium of a broad range of pathological conditions (inflammatory, malignant, autoimmune, infectious and hypoxic including infarctive/ischemic). ALCAM heterotypic ligand is CD6; a leukocyte membrane receptor expressed on monocytes, T cells and some B cells among other cells. The extracellular region of CD6 has three scavenger receptor cysteine rich (SRCR) domains that are connected to the membrane with a flexible stalk. The membrane proximal domain 3 of CD6 dock to the N-terminal domain 1 of CD166 in 1:1 stoichiometry and the stalk stabilizes this binding (Brown et al., 2015).

CD6 has an intricate 244 amino acids cytoplasmic signaling domain, which serves as an antenna for diverse signaling proteins in T cells and other immune cells. Proteomic analysis of the cholesterol rich transmigratory cup underscored ALCAM-CD6 co-interaction. This heterotypic binding co-opts in leukocyte diapedesis across the endothelium of pathological conditions and across the blood-brain barrier (BBB) and is remarkably amplified in autoimmune diseases such as Multiple Sclerosis, Graft versus Host Disease, autoimmune tissue damage and experimental autoimmune encephalomyelitis (EAE), for example. Moreover, ALCAM blockade successfully halted the transmigration of lymphocytes and monocytes across BBB endothelium.

Collectively, intriguing evidence indicate that ALCAM is a useful trafficking target for boosting the delivery of therapeutic cells (immune cell and other cell types), for example, to their intended pathological target(s).

BRIEF SUMMARY

Embodiments of the disclosure concern methods and compositions that enhance a targeted therapy for an individual. The targeted therapy may be of any kind, but in specific embodiments the therapy is an immunotherapy. The immunotherapy may be of any kind, but in specific cases the immunotherapy comprises cells, such as immune cells. The immune cells may be engineered to target a particular antigen, in at least certain cases, and in some embodiments the cells are engineered to have 1, 2, or more molecules (including chemokines, chemokine receptors, cytokines or cytokine receptors, chimeric antigen receptors for example) that facilitate targeting of the cells to a desired cell(s) or tissue(s). The cell(s) or tissue(s) may express one or more particular antigens. The antigen(s) may be of any kind, including a pathogen antigen or cancer antigen (such as a tumor antigen), for example. The pathogen may be of any kind, including a viral, bacterial, or fungal antigen. The disclosure encompasses any type of cell, of any origin (tissue origin, malignant/benign, hypoxic or inflamed and species), as well as cell derivatives (microsomes, membrane enclosures, or soluble molecules and others) and any complex non-cellular structure, such as corpuscles, micelles, liposomes. The disclosure further includes a soluble molecule facilitating this homing that can be used to prep the cells for targeted delivery by coating them prior to therapeutic usage.

Methods and compositions of the disclosure encompass enhanced targeted delivery of therapeutic complex biologic(s), including therapeutic and non-therapeutic cells, to pathological site(s) in an individual, including mammals such as humans. The pathological sites may be anywhere in the body, including within and/or outside of the blood-brain barrier (BBB).

In certain embodiments, the cells are immune cells used for therapy, such as adoptive cell transfer. In specific cases, the cells are T cells, B cells, NK cells, NKT cells, immortalized immune cells, dendritic cells and all types of antigen presenting cells, and phenotypic and molecular subsets of the aforementioned cells. The cells may include non-immune cells such as mesenchymal stromal cells, red blood cells, stem cells etc. The cells may be engineered cells that comprise an entity that targets ALCAM and in doing so facilitates targeting of the engineered cells to the desired cells or tissue. The immune cells may be modified to express a molecule that targets the T cells to desired cells or tissue, such as cells or tissue that express one or more antigens. In particular embodiments, the immune cells express a receptor that binds the antigen(s), such as chimeric antigen receptor (CAR) or transgenic T cell receptor (tgTCR). The receptor may be of any kind, including engineered chimeric antigen receptors, αβT cell receptors, chimeric cytokine receptors, cells engineered to express chemokines, resistance molecules, adhesion molecules and their ligands, homing molecules and their ligands, and cells making therapeutic entities such as enzymes, hormones and peptides and others. Access to the target tissue may require breaching of an endothelial/epithelial barrier using compositions of the disclosure. The disclosure further includes a soluble molecule facilitating this homing that can be used to prep the cells for targeted delivery by coating them prior to therapeutic usage.

In cases wherein the cell comprises a CAR, tgTCR or other targeting molecules, the CAR or tgTCR may be targeted to any antigen, including tumor antigens as an example. In specific cases, the CAR is specific for EphA2, HER2, GD2, Glypican-3, 5T4, 8H9, $\alpha_v\beta_6$ integrin, B cell maturation antigen (BCMA) B7-H3, B7-H6, CAIX, CA9, CD19, CD20, CD22, kappa light chain, CD30, CD33, CD38, CD44, CD44v6, CD44v7/8, CD70, CD123, CD138, CD171, CEA, CSPG4, EGFR, EGFRvIII, EGP2, EGP40, EPCAM, ERBB3, ERBB4, ErbB3/4, FAP, FAR, FBP, fetal AchR, Folate Receptor α, GD2, GD3, HLA-AI MAGE A1, HLA-A2, IL11Ra, IL13Ra2, KDR, Lambda, Lewis-Y, MCSP, Mesothelin, Muc1, Muc16, NCAM, NKG2D ligands, NY-ESO-1, PRAME, PSCA, PSC1, PSMA, ROR1, Sp17, SURVIVIN, TAG72, TEM1, TEM8, VEGRR2, carcinoembryonic antigen, HMW-MAA, VEGF receptors, and so forth. In Additionally, CAR T cells can be used in the context of autoimmunity either targeting an autoimmune antigen; known as chimeric autoantibody receptor (CAAR); or redirecting regulatory T cells to dampen the autoimmunity. In a specific embodiment, engineered CAAR that are reprogrammed to target autoimmune antigen (autoantibody) Dsg3 is helped in controlling the progression of the autoimmune disease Pemphigus vulgaris (PV). Also, human Tregs expressing (CAR) that targets the HLA class I molecule A2 were helpful in preventing GVHD Graft versus host diseases and transplants rejection. Therefore CAR cells can be used as a novel modulating immune agent based on the needed conditions.

Furthermore, new cellular therapy modalities are now used for pathological conditions such as Cancer and inflammation. For example, induced neural stem cells (iNSCs) engineered with optical reporters and therapeutic gene are identified now an efficacious therapeutic strategies for inflammatory degenerative disease as well as for brain cancer. Also, platelets and red blood cells are now recognized as useful bioagents for delivery for anti-thrombotic and anti-inflammatory agents. Therefore, cell therapy is a spurring treatment approach; yet the efficient homing to their intended target, especially in the brain, remains a challenge; and thus in particular embodiments platelets and red blood cells are modified by the claimed technology to achieve this aim.

In certain embodiments, therapy of any kind is enhanced to be able to access a target cell or tissue for the therapy by the therapy comprising a modification that facilitates binding to an adhesion molecule or its cognate hemophilic or heterophilic ligand. Although the modification facilitates binding to any adhesion molecule, in specific embodiments the adhesion molecule is ALCAM. In particular cases, the therapy is modified to have an ALCAM-binding moiety. The ALCAM-binding moiety can comprise any suitable moiety, but in specific cases the ALCAM-binding moiety comprises part or all of cluster of differentiation 6 (CD6). In cases wherein the ALCAM-binding moiety comprises part of CD6, the moiety may comprise at least one scavenger receptor cysteine rich (SRCR) domain and at least one stalk sequence, including at least one CD6 SRCR and at least one CD6 stalk sequence. In particular embodiments, the ALCAM-binding moiety comprises one or more iterations of a CD6 SRCR linked to a CD6 stalk (the ALCAM minimal binding ELEMENT (MBE). In some cases the ALCAM-binding moiety comprises 1, 2, 3, 4, 5, 6, 7, 8, 9, 10, or more ALCAM MBE.

In particular embodiments, the therapy comprises at least one MBE and in some cases the MBR is also linked to other domains. In cases wherein the MBE is part of a molecule expressed by a cell, the molecule may be a receptor, including a receptor on a cell, the MBE may be operably linked to any kind of a transmembrane domain and one or more endodomains in relation to the configuration of a cell, in certain cases.

Embodiments include polynucleotides and encoded protein sequences that comprise, consist of, or consist essentially of 1, 2, 3, 4, 5, 6, 7, 8, 9, 10, or more CD6 scavenger receptor cysteine rich (SRCR) domains and 1, 2, 3, 4, 5, 6, 7, 8, 9, 10 or more CD6 stalks.

Embodiments include polynucleotides and encoded protein sequences that comprise, consist of, or consist essentially of 1, 2, 3, 4, 5, 6, 7, 8, 9, 10, or more CD6 scavenger receptor cysteine rich (SRCR) domains and 1, 2, 3, 4, 5, 6, 7, 8, 9, 10 or more CD6 stalks in a secreted form or in a preparation that can be used to prime the therapeutic cell prior to administration.

ALCAM minimal binding MBE ["CD6 and stalk"] expression on immune cells can enhance ALCAM-specific targeted delivery of therapeutic complex biologics to pathological sites, including across the BBB.

In certain embodiments, the delivery platform encompasses molecular features that enable stronger and/or weaker interaction that can be more specific than that described above (D3 and stalk) at the endothelium interface. The methods and compositions of the present disclosure can harness the binding to endothelial receptors belonging to cell adhesion molecules (CAMs) family to enhance the clustering at the transmigratory cup. Thus, in addition to binding to ALCAM via CD6 domains, the delivery platform may include β2 integrin CD11b/CD18 (known as LFA-1 or MAC-1), which can bind to ICAM-1 and JAM-1 on endothelium. Also, it might include alpha4beta1 integrin, known as VLA-4, which can bind to vascular VCAM-1, as well as beta7 integrin LPAM-1 (alpha4/beta7) that binds to Addressin and GLYCAM-1 on the membrane of high endothelial venules. Furthermore, incorporating L-selectin that binds to E-selectins and P-selectins on the endothelium increases the tethering over the vessel wall and eventually entitles the effective migration through the vasculature towards the intended target, in at least some embodiments. Therefore, embodiments of the disclosure have global molecular keys for interacting with and breaching the endothelial/epithelial barrier and/or the endothelial/epithelial blood brain barrier to achieve advantageous delivery kinetics for any therapeutic product. In addition to the aforementioned molecules, those molecules in the same class with the same function, and or portions thereof, are encompassed herein.

In one embodiment, there is a composition (for use at least in therapeutic or diagnostic (such as imaging) comprising a) at least one therapeutic moiety; said moiety operably linked to b) an activated leukocyte adhesion molecule (ALCAM)-binding moiety, wherein the ALCAM-binding moiety comprises at least one cluster of differentiation 6 (CD6) scavenger receptor cysteine rich (SRCR) domain and at least one CD6 stalk domain. In specific cases, the composition comprises 1, 2, 3, 4, 5, or more ALCAM-binding moieties. As an example, the therapeutic moiety may comprise a cell, cell derivative, small molecule, protein, peptide, nucleic acid, viral genome or coat, exosomes, dendrimers, biomimic nanoparticles, micelles, liposomes, or combination thereof. The moieties could also be secreted or purified moieties in a preparation that can be used to prime the cells for targeted delivery. The cell may be an immune cell (T cell, NK cell, NK T cell, B cell, Th17, dendritic cell, or T regulatory cell), stem cell (hematopoietic stem cell or mesenchymal stem cell or embryonic stem cell), mesenchymal stromal cell (MSC), or hybridoma. In cases wherein a cell derivative is employed, the cell derivative may be a corpuscle (for example, red blood cell or platelet) or microsome. In specific embodiments, any binding moiety encompassed by the disclosure enables any composition for binding without having an effect of its own.

In specific embodiments, an ALCAM-binding moiety is configured as at least part of an ectodomain of a cell receptor or an adhesion molecule, such as ICAM or VCAM. A cell receptor may comprise a transmembrane domain and at least one endodomain, such as an ALCAM endodomain. The endodomain may be truncated or mutated. In some cases, the receptor lacks an endodomain. A cell receptor may be a chimeric antigen receptor, a chimeric cytokine receptor, an αβT cell receptor, a chemokine receptor, or any other anchoring protein, for example.

A cell comprising any therapeutic composition encompassed by the disclosure are included. The cell may be comprised in a plurality of cells and a combination thereof. The cell may be an immune cell (T cell, NK cell, NK T cell, T cell, NK cell, NK T cell, B cell, Th17, dendritic cell, or T regulatory cell), stem cell, mesenchymal stromal cell (MSC), a somatic or germinal (gonadal) cell or hybridoma. In certain cases, the ALCAM-binding moiety is configured as at least part of an ectodomain of a cell receptor, which may or may not comprise a transmembrane domain and at least one endodomains and the modification thereof. Cells may comprise one or more of a chimeric antigen receptor, a chimeric cytokine receptor, an αβT cell receptor, a chemokine receptor or any other anchoring protein.

In one embodiment, there is a method of providing a therapeutic moiety to an individual, comprising the step of delivering an effective amount of a therapeutic composition as encompassed herein to the individual or an effective amount of any one of cells as encompassed herein to the individual. The individual may be in need of therapy that targets desired particular cell(s) or tissue(s) comprising particular cell(s) in the individual. The particular cells may be ALCAM-expressing pathological endothelial cells, including within the blood-brain barrier or blood tumor, blood hypoxic, blood inflammatory and blood infarctive area interface. In specific embodiments, the individual has a medical condition selected from the group consisting of cancer, pathogen infection, experimental autoimmune encephalomyelitis, brain abscess, epilepsy, multiple sclerosis, Alzheimer's Disease, cerebral edema, cerebral ischemia, prion diseases, encephalitis, or inflammation.

In a certain embodiment, there is provided a therapeutic composition comprising a) at least one therapeutic moiety; said moiety operably linked to one or more of b) adhesion molecule binding moiety. The adhesion molecule binding moiety may be a binding moiety for ALCAM, ICAM-1, JAM-1, VCAM-1, Addressin, or GLYCAM-1. An example of a binding moiety for ICAM-1 comprises part or all of MAC-1 and/or part or all of LFA-1. An example of a binding moiety for JAM-1 comprises part or all of MAC-1 and/or part or all of LFA-1. An example of a binding moiety for VCAM-1 comprises part or all of VLA-4. An example of a binding moiety for GLYCAM-1 comprises part or all of LPAM-1. An example of a binding moiety for Addressin comprises part or all of LPAM-1.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIGS. 1A and 1B. FIG. 1A shows ALCAM expression in glioblastoma (GBM) endothelium; (FIG. 1B) ALCAM is upregulated in the vascular and perivascular region;

FIG. 2 shows ALCAM expression in pathological endothelium; ALCAM is expressed on tumor endothelium isolated from surgical specimen and characterized for ubiquitous endothelial markers;

FIGS. 5A and 5B concern illustrations of an embodiment of D3 Artificial receptor Design. FIG. 5A shows mapping the Minimal binding Element (MBE) to ALCAM and FIG. 5B shows an embodiment of artificial homing receptor design and illustrations of the binding Different ALCAM-binding entity-bearing constructs;

FIGS. 10A and 10B show the average adhesion percentage per microscopic field on a monolayer of ALCAM+ tumor brain endothelium (pre-activated with 10 μg/ml TNF alpha). Transduced D3 T cells simultaneously with Non-transduced control T cells were injected to Bioflux channels at a density of 1×10$^6$ cells/ml in test media. Shear was adjusted during the experiment from 3 to 1 dyne/cm$^2$ using the BioFlux 200 controller. Movies of cell adhesion were captured with an exposure time of 100 ms at 500 ms intervals (A stack of thirty consecutive images were captured 0.5 seconds apart (100 ms exposure). Fraction of stationary cells were counted per field of view (n=10) using ImageJ software. D3 multimerization increases the adhesion ability to ALCAM+ cells (5D3>3D3>1D3) while D3 signaling domain significantly saturates the adhesion propriety of all D3 engineered cells regardless the exodomain number. FIG. 10B is the dynamic adhesion percentage of D3 T cells on ALCAM+ cells over time. One hour movie of cell adhesion was captured. Optical images of T cells on ALCAM+ endothelial cells at the endpoint of each time point were taken. Bar=100 μm. Normalized adhesion percentage was plotted vs different time point at same shear force (2 dyne/cm²). the dynamic adhesion results coincide with the static adhesion values; affirming that D3 increases cell adhesion propriety to ALCAM positive target. Data were analyzed by two-way ANOVA and Tukey's post hoc test; three repeated experiments were done in the VA lab in BCM. Error bars are STEV; * P<0.05, P<0.01, *P<0.001.

FIG. 21 (SEQ ID NO:13) shows an example of a construct used for cloning to produce a gene product comprising an ALCAM-binding moiety, including a CD6 Minimal Binding Element for ALCAM (also referred to as a MBE). This figure shows the CD6 MBE monomer truncated including a secretory domain (gray text), domain 3 of the three SRCR domains (single underlined), a stalk (dash underline), and a transmembrane domain (bolded with no underline);

FIG. 22 (SEQ ID NO:14) provides an example of a construct used for cloning to produce a gene product comprising an ALCAM-binding moiety, including a CD6 MBE monomer with a signaling domain. This figure shows the CD6 MBE monomer with a secretory domain (gray text), domain 3 of the three SRCR domains (single underlined), a stalk (dash underline), a transmembrane domain (bolded with no underline), and a signaling domain (italics);

FIG. 23 (SEQ ID NO:15) provides an example of a construct used for cloning to produce a gene product comprising an ALCAM-binding moiety, including a CD6 MBE trimer that is truncated. This figure shows the CD6 MBE monomer with a secretory domain (gray text), domain 3 of the three SRCR domains (single underlined), a stalk (dash underline), and a transmembrane domain (bolded with no underline);

FIG. 24 (SEQ ID NO:16) provides an example of a construct used for cloning to produce a gene product comprising an ALCAM-binding moiety, including a CD6 MBE trimer with signaling. This figure shows the CD6 MBE monomer with a secretory domain (gray text), domain 3 of the three SRCR domains (single underlined), a stalk (dash underline), a transmembrane domain (bolded with no underline), and a signaling domain (italics);

FIG. 25 (SEQ ID NO:17) provides an example of a construct used for cloning to produce a gene product comprising an ALCAM-binding moiety, including a CD6 pentamer truncated (no signaling domain). This figure shows the CD6 MBE monomer with a secretory domain (gray text), domain 3 of the three SRCR domains (single underlined), and a stalk (dash underline);

FIG. 26 (SEQ ID NO:18) provides an example of a construct used for cloning to produce a gene product comprising an ALCAM-binding moiety, including a CD6 MBE pentamer with signaling. This figure shows the CD6 MBE monomer with a secretory domain (gray text), domain 3 of the three SRCR domains (single underlined), a stalk (dash underline), a transmembrane domain (bolded with no underline), and a signaling domain (italics);

FIG. 27A. Representative images of the in vivo bioluminescence imaging (BLI) of GFP ffluc+ T cells in the brain shown as the mean radiance (photons/second/cm2/selected region), where n=10 per test group and n=5 per control. GBM orthotopic models were established in mice then at day 12, and 10·10^6 T cells tagged with GFP ffluc IV were injected (n=10) as either Test group 1-D3 modified T cells or a control non-transduced (NT) group. Their luceferin BLI signals were detected at different time points after injection (6 hrs, 24 hr, 48 hrs, 6 days, 8 days). FIG. 27B. Graph represents the fold change in the BLI of Test group 1-D3 in relation to control group. 1-D3 T cells have significant higher BLI in comparison with NT control T cells after 24 and 48 hrs. Data were analyzed by two-tailed student T test; Error bars are ±STEV; * P<0.05, P<0.01, *P<0.001;

FIG. 28A. Representative images of the in vivo bioluminescence imaging (BLI) of GFP ffluc+ T cell in the brain shown is the mean radiance (photons/second/cm2/selected region), where (n=10 per test group and n=5 per control). GBM orthotopic model were established in mice then at day 12, 10·10^6 T cells tagged with GFP ffluc IV were injected (n=10) either Test group 1-D3 Δ-modified T cells or control Non transduced (NT) group. Their luceferin BLI signals were detected in different time points after injection (6 hrs, 48 hrs, 6 days) FIG. 28B. Graph represents the fold change in the BLI of Test group 1-D3 in relation to control group. 1-D3Δ-modified (truncated) T cells have significant higher BLI in comparison with NT control T cells after 24 and 48 hrs. Data were analyzed by two-tailed student T test; Error bars are ±STEV; * P<0.05, P<0.01, *P<0.001;

FIGS. 29A, 29B, and 29C show D3 T cell successful homing and infiltration in the tumor after 24 hrs IV administration. FIG. 29A. Flow cytometric comparison of D3(MBE) transduced T cells infiltrates gated in CD3+ CD45+ subsets in the tumor explants vs. control NT cells. T cells were injected IV and after 24 hrs, the mice were euthanized and T cell infiltrates that were either D3 Test or NT were isolated using Percol/Ficoll and then stained with CD3-PerCP and CD45-APC and D3-PE for an hour. Analyses were done using Flowjo software. FIG. 29B. Graph represents percentage of human CD3 CD45 cells in GBM explants isolated from SCID mice. FIG. 29C. Percentage of CD6 D3+ transduced cells gated in the CD3+CD45+ subset. There is a high significance in D3 T cells homing to tumor and infiltration capacity compared to NT control T cells. Data were analyzed by 2-tailed Student T-test; Error bars are STEV; * P<0.05, P<0.01, *P<0.001. (n=5);

FIGS. 31A-31E show D3 (MBE) role in the mechanical stabilization of the migrating cells. Cells were fixed in 4% parafoladehyde then permealized with ice cold methanol; then stained with FAK lry antibody followed by secondary ALexa fluor 488, the incubated with Phalloindin Texas Red, then DAPI nuclear staining. FIGS. 31A-31E staining of F-Actin/focal adhesion Kinase (FAK) that are essential for the cytoskeleton organization of the migrating cells and mediate efficient invasion capacity over ALCAM+ endothelium. FIG. 31A shows the colocalization of F-actin and FAK in MBE cells in comparaison to control cells. FIG. 31B shows Total internal Reflection fluorescence TIRF imaging at 60× where the high resolution of F-actin induction at D3/ALCAM interface is significantly detected. FIG. 31C quantification MFI-Actin on the cell surface using FIJI software, F-actin intensity n MBE cells is highly significant in comparison to NT T cells. FIG. 31D represents the Structural illuminating Microscopy SIM at 60× image of MBE T cells after ALCAM interaction. It shows the invadopodia and the actin raffle with the focal adhesions that mediate T cells endothelial invasion. FIGS. 31E and 31F show TIRF imaging at 60× of the stretch induced Focal adhesion Kinases (FAK). MBE T cells has higher FAK intensity that enable them to protrude and invade the endothelial/epithelial Barrier.

DETAILED DESCRIPTION

Figure 3:
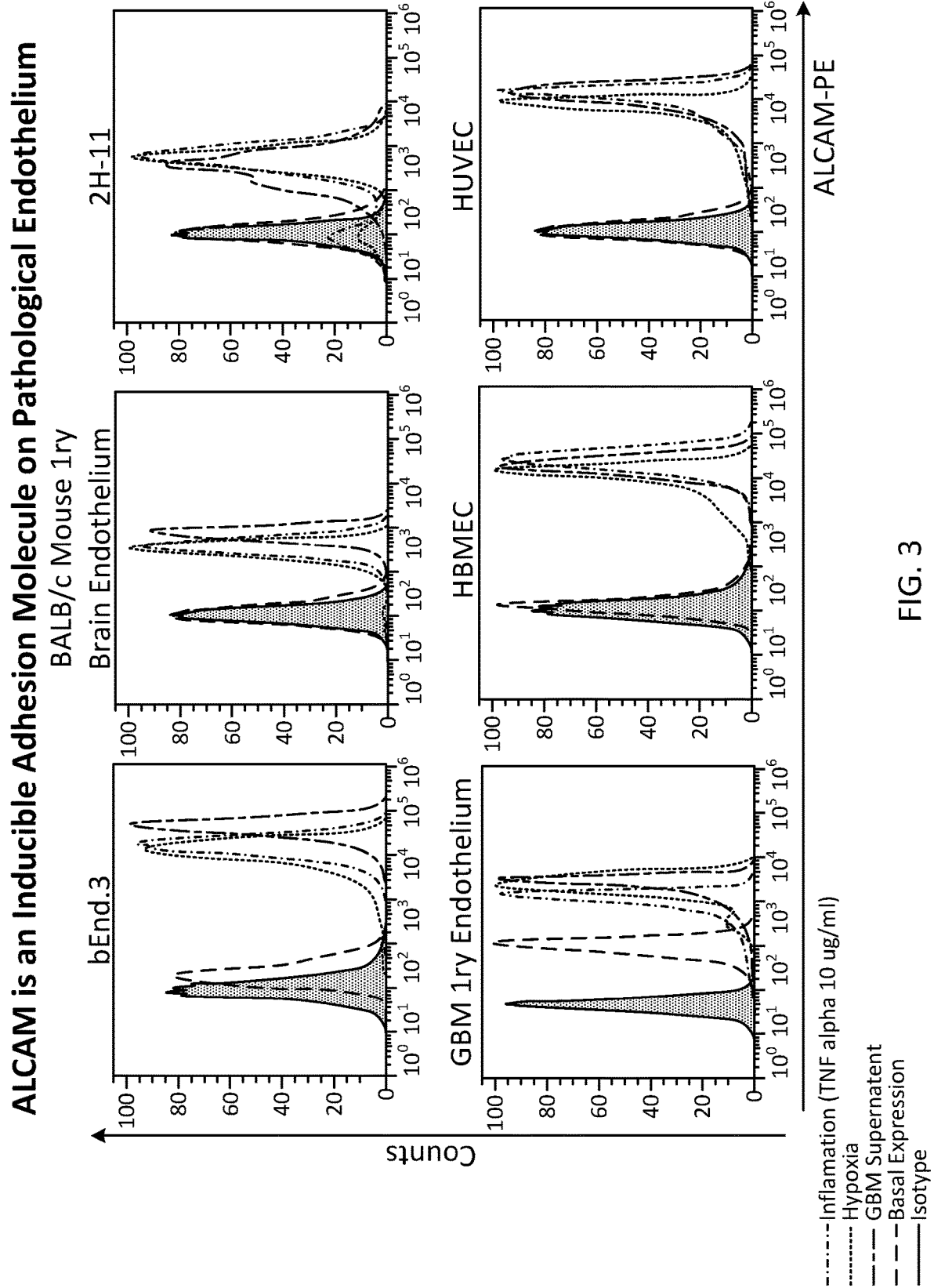
FIG. 3 shows FACS analysis for ALCAM expression in three different pathological conditions (malignancy (red line), inflammation (blue line) and hypoxia (black line))

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the invention may "consist essentially of" or "consist of" one or more sequences of the invention, for example. Some embodiments of the invention may consist of or consist essentially of one or more elements, method steps, and/or methods of the invention. It is contemplated that any method or composition described herein can be implemented with respect to any other method or composition described herein. The scope of the present application is not intended to be limited to the particular embodiments of the process, machine, manufacture, composition of matter, means, methods and steps described in the specification.

Immunosurveillance of the central nervous system (CNS) is tightly regulated by a molecular network that directs cell migration across BBB. The success of leukocyte trafficking from blood into tissues depends on complementary endothelial homing molecule interactions acting in a concerted and specific manner. At the BBB, there is a dynamic state of homing molecule expression that becomes disrupted during pathological conditions. Indeed, disruption of the regulation of these molecules compromises the capture of T cells from the blood stream, impeding effective adoptive cell therapy. Findings from infiltrative brain diseases may be exploited to overcome this roadblock. Upregulation of ALCAM was previously shown to be the initial point of T cell anchorage to the endothelium of the BBB. ALCAM was found to co-localize to the T cell surface molecule CD6 in the trans-migratory cup during diapedesis through the BBB. ALCAM/CD6 crosslinking may trigger the upregulation of T cell ligands to a number of other endothelial adhesion molecules, resulting in a second wave of tight adhesion that leads to T cell capture, rolling, arrest, crawling and diapedesis. In the brain tumor endothelium this essential second wave of molecules was completely absent. Embodiments of the disclosure address the failure of T cell homing to brain tumors and proposes a novel solution. Embodiments of the disclosure provide introduction of a cellular platform powered by the molecular key for breaching the BBB, ALCAM, to enable the migration of adoptively transferred T cells across the BBB. This strategy challenges current paradigms of brain tumor vascular "anergy" by revealing the vascular interactome profile and comparing that condition to infiltrative CNS diseases such as multiple sclerosis (MS) and experimental autoimmune encephalitis. Further, the role of the ALCAM/CD6 axis during T cell trans-endothelial migration though the BBB is addressed. The results of these studies shed light on the T cell/endothelium interaction, uncovering mechanisms of failed egress of cellular therapies to the brain. One can generate an impactful translational brain delivery tool that exploits this axis to regain the adhesive capacity of T cells, but also other immune and non-immune system cells, to anergic endothelial cells. Introducing a cellular platform to deliver complex biologics to the CNS is a modular innovation that improves broad therapeutic applications such as chimeric antigen receptor T cells for cancer, virus specific T cells for infections, Tregs for autoimmunity or graft vs. host disease, as well as other complex biologics to the neuroaxis.

I. Compositions Comprising ALCAM-Binding Moieties

In particular embodiments there is a composition that comprises one or more ALCAM-binding moieties. The composition may be of any kind, but in specific embodiments the composition is a therapeutic but could be a diagnostic composition. The therapeutic composition may be of any kind, but in specific embodiments it comprises a cell, protein, drug, peptide, nucleic acid, nanocapsules, dendrites, virus protein or lipid membrane, exososmes, liposomes and any complex or simple molecular formation as well as a combination thereof, and so forth. In cases wherein the therapeutic composition is a cell, the cell may be of any kind, but in specific cases the cell is an immune cell, such as a T cell, NK cell, NKT cell, immune cells (T cell, NK, B cell for Ab production, Tregs, MSDCs) or other cells such as hematopoietic stem cell, Platelet, RBCs, mesenchymal stem cells, or any of the aforementioned functional per se or as a delivery system and so forth. The ALCAM-binding moieties could be in a secreted form by the cell platform or in a preparation form and can be used to prime cells targeted to pathological sites.

An ALCAM-binding moiety comprises at least one CD6 SRCR domain, such as the third domain in wildtype CD6 that is most proximal to the membrane, and comprises a stalk sequence. In some cases, a therapeutic composition comprises one SRCR domain 3 and one stalk, although in other cases there are 2 of each, 3 of each, 4 of each, 5 of each, 6 of each, 7 of each, 8 of each, 9 of each, 10 of each, and so forth. In particular cases, there is a pair that includes one CD6 SRCR domain immediately adjacent to a CD6 stalk, and one or more pairs of this bipartite domain may be included in the ALCAM-binding moiety. In certain cases other binding regions of CD6 and or stalks and or other regions could be employed singly, in multimer form or in combination with other regions to bind an entity of endothelial cells. In certain cases at least, there are repeating iterations of SRCR domain and CD6 stalk in a single molecule. In a polypeptide oriented from N-terminus to C-terminus, a SRCR domain may be N-terminal to a stalk, although in alternative embodiments a SRCR domain is C-terminal to a stalk. In particular aspects a transmembrane domain is C-terminal to a stalk sequence or is C-terminal to a pair comprising a SRCR domain and a stalk.

In some cases, domains other than the ALCAM-binding moiety (one SRCR and one stalk) may be utilized, such as a secretory signal, transmembrane domain and, optionally, at least one stimulation domain. An ALCAM-binding moiety (one SRCR and one stalk, at least) might include any domain(s) that enhance the interaction stiffness (decreases the dissociation constant (Kd) of the molecule). It can encompass one or more multiple endodomains can be downstream linked with flexible glycine serine hinge. Other components include any of or combination of the following: structural molecules including their anchoring proteins, adhesion molecules and their receptors including their anchoring elements and proteins, chemokine receptors, cytokine receptors including their signaling domains, T cell receptor elements and other components of lipid rafts involved in cell/cell interaction.

Although CD6 SRCR domain is employed, in some cases other components of the ALCAM-binding moiety or compositions comprising same utilize components from molecules other than CD6 or bind to adhesion molecules other than ALCAM (such as ICAM and VCAM). For example, although CD6 stalk may be used in particular aspects of the disclosure, in other cases the stalk is from a protein other than CD6. Although CD6 transmembrane domain may be used in particular aspects of the disclosure, in other cases the transmembrane domain is from a protein other than CD6.

In specific embodiments, a construct that comprises one or more ALCAM-binding moieties comprises one or more endodomains that may or may not be stimulatory domains. In certain cases the endodomain for the composition is the CD6 endodomain, although in other cases part or all of an endodomain for another molecule are used instead of or in conjunction with the CD6 endodomain. Although any stimulatory domain or combinations of stimulatory domains may be utilized with the ALCAM-binding moieties, in specific cases the stimulatory domain is CD28, 4-1BB, OX40, ICOS, other signaling domains, and domains of chemokine receptors and adhesion molecules and their cognate receptors or a combination thereof.

The ALCAM-binding moiety may be affixed to the composition by any means. In cases wherein the therapeutic composition is a cell, the ALCAM-binding moiety may be expressed by the cell. A single cell may express multiple ALCAM-binding moieties. A cell may harbor a polynucleotide that expresses the ALCAM-binding moiety. In cases wherein the therapeutic composition is not a cell, the ALCAM-binding moiety may be attached to the therapeutic composition covalently or non-covalently. Such structures include biomimic nanoparticules such as cell membrane-camouflaged nanoparticles with MBR that are bearing the drug or the deliverable material inside or dendrimers/nanocapsule dendrites with MBR and so forth.

FIGS. 21-26 provide examples of constructs that may be employed that comprise at least one ALCAM-binding moiety. In FIG. 21, there is a construct that comprises a secretory signal, one CD6 MBE with a transmembrane domain and without a signaling domain. FIG. 22 demonstrates a construct that comprises a secretory signal, one CD6 MBE with a transmembrane domain and with a signaling domain. FIG. 23 illustrates a construct with a secretory signal, three CD6 MBE domains with a transmembrane domain and without a signaling domain. FIG. 24 shows a construct with a secretory signal, three CD6 MBE domains with a transmembrane domain and with a signaling domain. In FIG. 25, there is a construct with a secretory signal, five CD6 MBE domains with a transmembrane domain but without a signaling domain. In FIG. 26, there is a construct with a secretory signal, five CD6 MBE domains with a transmembrane domain but with a signaling domain.

Figure 5B:
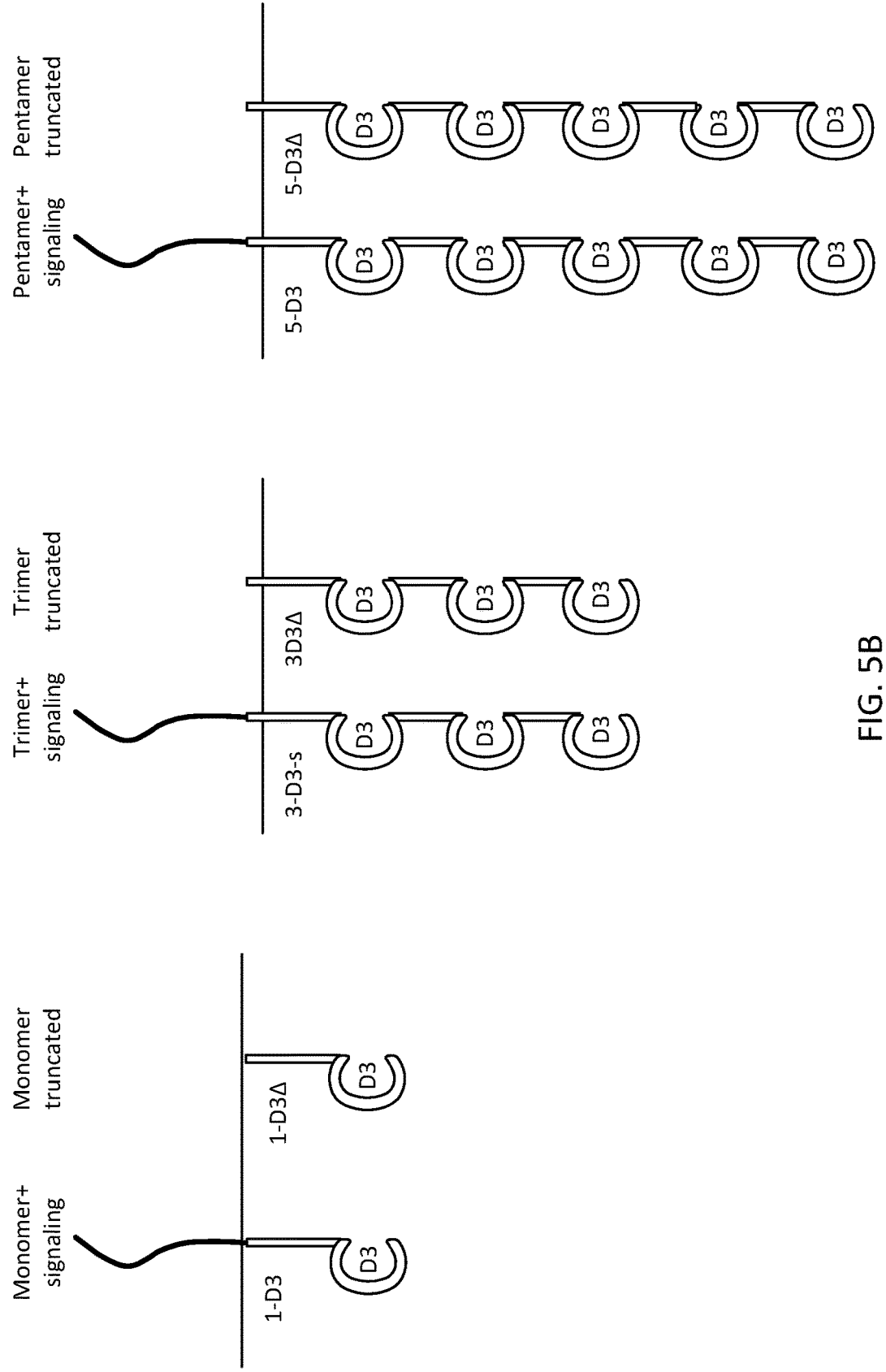
Figure 6:
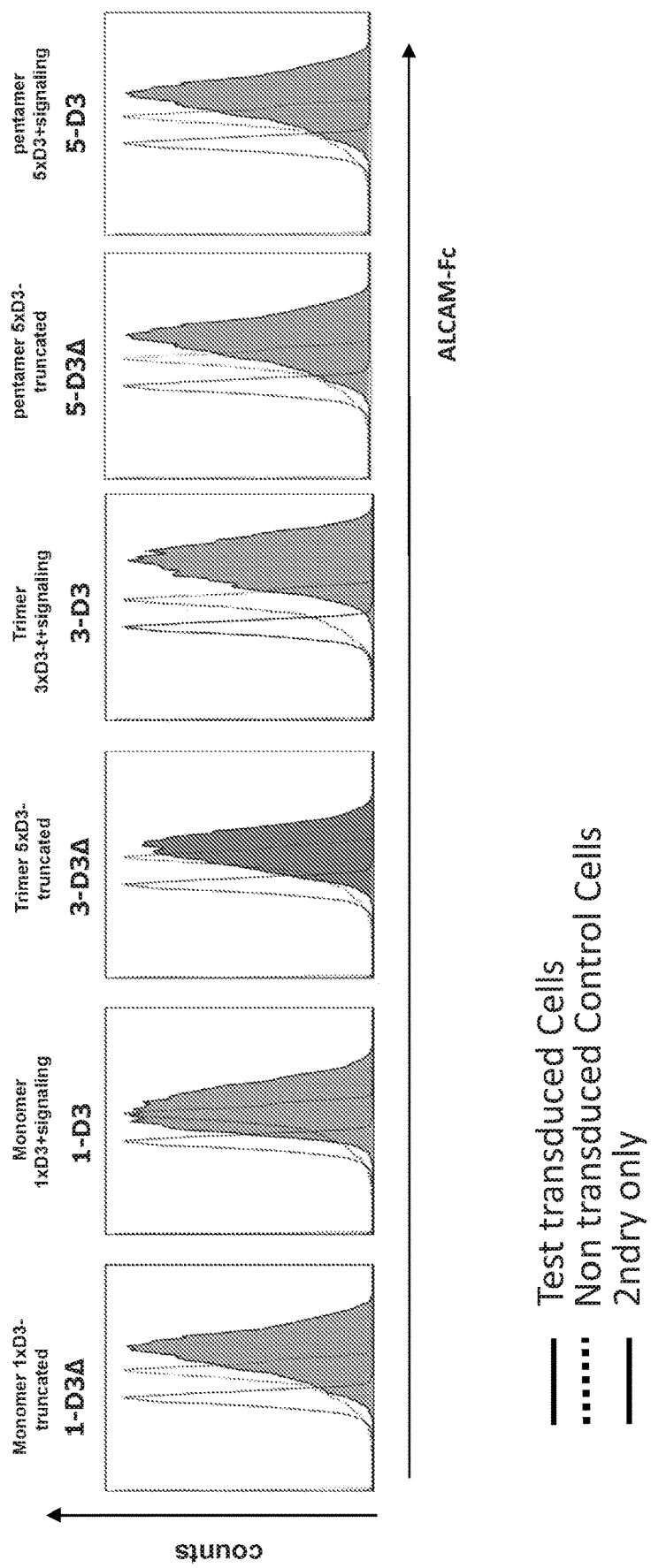
FIG. 6 is a FACS analysis to confirm ALCAM specific binding to MBE D3 receptors on the surface of primary T cells; it shows the successful D3 artificial receptor expression on T cells surface using ALCAM-fc.
Figure 7:
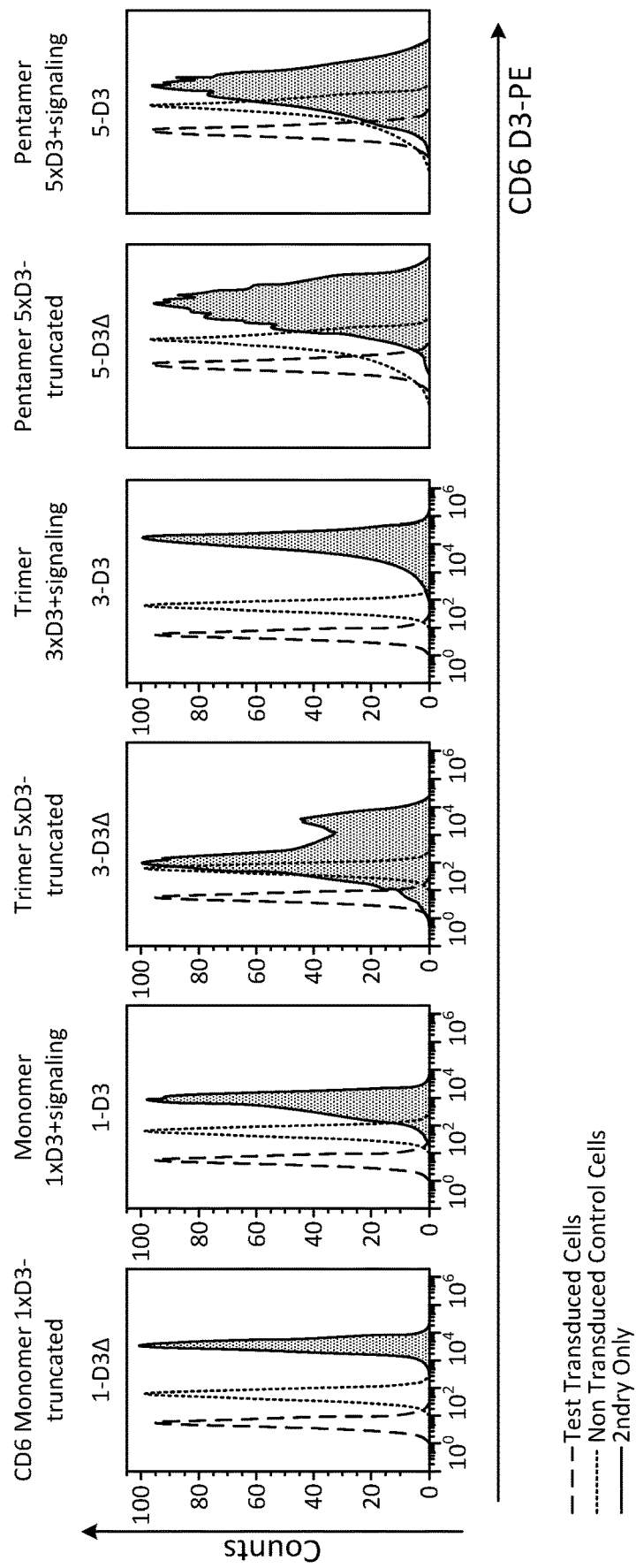
FIG. 7 is a FACS analysis of the successful (MBE) D3 artificial receptor expression on T cells surface using a specific mAb for domain 3 of CD6.
Figure 8:
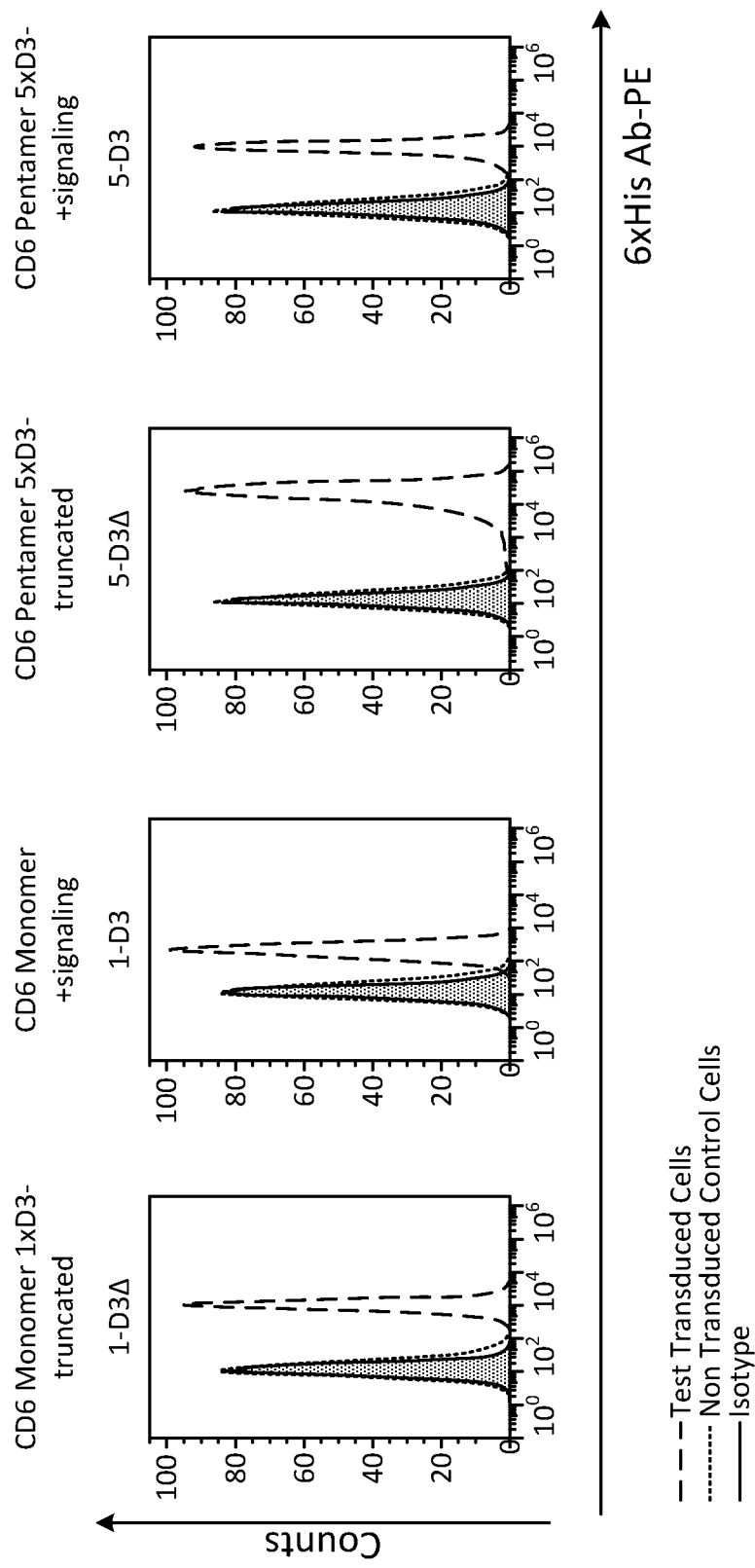
FIG. 8 is a FACS analysis for another way to detect the D3 expression using a specific mAb for 6× His TAG. Cells were incubated with primary mouse 6× His mAb conjugated to PE (filled red histogram)

Examples of particular molecules such as those illustrated in FIGS. 5A and 5B are encompassed in the disclosure. An example of the sequence of a secretory signal includes ATGTGGCTCTTCTTCGGGATCACTGGATTGCTGACGGCAGCCCTCTCAGGT (SEQ ID NO:1). Others include ValVal-Leu-Gly-Lys-Lys-Gly-Asp-Xaa-Val-Glu-Leu (SEQ ID NO:6) and any natural or artificial secretory domains, also known as leader sequences.

An example of a SRCR sequence (domain 3) is (SEQ ID NO: 2)
TGGCGCCTGACAGGGGGCGCTGACCGCTGCGAGGGGCAGGTGGAGGTACA

CTTCCGAGGGGTCTGGAACACAGTGTGTGACAGTGAGTGGTACCCATCGG

AGGCCAAGGTGCTCTGCCAGTCCTTGGGCTGTGGAACTGCGGTTGAGAGG

CCCAAGGGGCTGCCCCACTCCTTGTCCGGCAGGATGTACTACTCATGCAA

TGGGGAGGAGCTCACCCTCTCCAACTGCTCCTGGCGGTTCAACAACTCCA

ACCTCTGCAGCCAGTCGCTGGCAGCCAGGGTCCTCTGCTCA.

The sequence of the SRCR domain 3 is as follows: Met Y Y S C N G E E L T L S N C S W R F N N S N L C S Q S L A A R V L C S A S R S L H N L S T P E V P A S V Q T V T I E S S V T V K I E N K E S R E L (SEQ ID NO:7).

Also it might include SRCR domain 1 and 2 and 3 with the following as:

(SEQ ID NO: 8)
MWLFFGITGLLTAALSGHPSPAPPDQLNTSSAESELWEPGERLPVRLTNG

SSSCSGTVEVLEASWEPACGALWDSRAAEAVCRALGCGGAEAASQLAPPT

PELPPPPAAGNTSVAANATLAGAPALLCSGAEWRLCEVVEHACRSDGRRA

RVTCAENRALRLVDGGGACAGRVEMLEHGEWGSVCDDTWDLEDAHVVCRQ

LGCGWAVQALPGLHFTPGRGPIHRDQVNCSGAEAYLWDCPGLPGQHYCGH

-continued
KEDAGAVCSEHQSWRLTGGADRCEGQVEVHFRGVWNTVCDSEWYPSEAK

VLCQSLGCGTAVERPKGLPHSLSGRMYYSCNGEELTLSNCSWRFNNSNLC

SQSLAARVLCSASRSLHNLSTPEVPASVQTVTIESSVTVKIENKESRELM

LLIPSIVLGILLLGSLIFIAFILLRIKGKYALPVMVNHQHLPTTIPAGSN

SYQPVPITIPKEVFMLPIQVQAPPPEDSDSGSDSDYEHYDFSAQPPVALT

TFYNSQRHRVTDEEVQQSRFQMPPLEEGLEELHASHIPTANPGHCITDPP

SLGPQYHPRSNSESSTSSGEDYCNSPKSKLPPWNPQVFSSERSSFLEQPP

NLELAGTQPAFSAGPPADDSSSTSSGEWYQNFQPPPQPPSEEQFGCPGSP

SPQPDSTDNDDYDDISAA

An example of a stalk sequence is GCTTCCCGGAGTTTGCACAATCTGTCCACTCCCGAAGTCCCTGCAAGTGTTCAGACAGTCACTATAGAATCTTCTGTGACAGTGAAAATAGAGAACAAGGAATCTCGGGAGCTAATGCTCCTC (SEQ ID NO:3). In some cases instead of a stalk a linker such as glucine serine "GS" linker or KESGSVSSEQLAQFRSLD (SEQ ID NO:9) linker or rigid linker like A(EAAAK)$_n$A (SEQ ID NO:10) may be employed, depending on the cellular delivery context or inert delivery context.

An example of a transmembrane domain sequence is ATCCCCTCCATCGTTCTGGGAATTCTCCTCCTTGGCTCCCTCATCTTCATAGCCTTCATCCTC (SEQ ID NO:4) having a protein sequence of Met L L W R L T G G A D R C E G Q V E V H F R G V W N T V C D S E W Y P S E A K V L C Q S L G C G T A V E R P K G L P H S L S G R (SEQ ID NO:11). However, any transmembrane domain sequence may be utilized.

An example of a signaling domain is TTGAGAATTAAAGGAAAATATGCCCTCCCCGTAATGGTGAACCACCAGCACCTACC CACCACCATCCCGGCAGGGAGCAATAGCTATCAACCGGTCCCCATCACCATCCCCA AAGAAGTTTTCATGCTGCCCATCCAGGTCCAGGCCCCGCCCCCTGAGGACTCAGACT CTGGCTCGGACTCAGACTATGAGCACTATGACTTCAGCGCCCAGCCTCCTGTGGCCC TGACCACCTTCTACAATTCCCAGCGGCATCGGGTCACAGATGAGGAGGTCCAGCAA AGCAGGTTCCAGATGCCACCCTTGGAGGAAGGACTTGAAGAGTTGCATGCCTCCCA CATCCCAACTGCCAACCCTGGACACTGCATTACAGACCCGCCATCCCTGGGCCCTCA GTATCACCCGAGGAGCAACAGTGAGTCGAGCACCTCTTCAGGGGAGGATTACTGCA ATAGTCCCAAAAGCAAGCTGCCTCCATGGAACCCCCAGGTGTTTTCTTCAGAGAGGA GTTCCTTCCTGGAGCAGCCCCCAAACTTGGAGCTGGCCGGCACCCAGCCAGCCTTTT CAGCAGGGCCCCCGGCTGATGACAGCTCCAGCACCTCATCCGGGGAGTGGTACCAG AACTTCCAGCCACCACCCCAGCCCCCTTCGGAGGAGCAGTTTGGCTGTCCAGGGTCC CCCAGCCCTCAGCCTGACTCCACCGACAACGATGACTACGATGACATCAGCGCAGC C (SEQ ID NO:5) having an amino acid sequence of: Met L P I Q V Q A P P P E D S D S G S D S D Y E H Y D F S A Q P P V A L T T F Y N S Q R H R V T D E E V Q Q S R F Q Met P P L E E G L E E L H A S H I P T A N P G H C I T D P P S L G P Q Y H P R S N S E S S T S S G E D Y C N S P K S K L P P W N P Q V F S S E R S S F L E Q P P N L E L A G T Q P A F S A G P P A D D S S S T S S G E W Y Q N F Q P P P Q P P S E E Q F G C P G S P S P Q P D S T D N D D Y D D I S A A G S (SEQ ID NO:12). However, any signal domain or stimulatory domain and/or safety switch may be utilized.

Sequences for any particular part of a molecule may be 100% identical to a wildtype sequence, including sequence for a SRCR domain, stalk, transmembrane domain, and/or secretory signal. It may also be altered to optimize its functionality. Thus, in specific cases the sequence of a secretory signal, SRCR domain, stalk sequence, transmembrane domain, or signaling domain is 100% identical or less than 100% identical to its respective wildtype sequence. In certain cases, the sequence(s) are modified compared to their respective wildtype sequences, regardless of whether or not the sequence is the nucleotide sequence or its corresponding protein sequence. Some mutations can be included to enhance the SCRC binding affinity to ALCAM (Brown et al, 2016). In some cases, a particular sequence in the composition may be 99, 98, 97, 96, 95, 94, 93, 92, 91, 90, 85, 80, 75, 70, or less percent identical to its corresponding wildtype counterpart. In some embodiments, the sequence of a secretory signal is that of SEQ ID NO:1, although sequences that are 99, 98, 97, 96, 95, 94, 93, 92, 91, 90, 85, 80, 75, 70, or less percent identical to SEQ ID NO:1 are utilized in the compositions.

In certain embodiments, the ALCAM-binding moiety of the composition is configured as at least part of an ectodomain of a cell receptor, including a cell receptor on an immune cell. In particular cases the cell receptor comprises a transmembrane domain and at least one endodomain, and in specific cases the cell receptor is a chimeric antigen receptor, a chimeric cytokine receptor, an αβT cell receptor, cognate molecule for a therapeutic, homing or activating entity, chemokine receptor, or integrin receptor, for example.

II. Alternatives to ALCAM-Binding Moieties

In some embodiments, other than the therapeutic composition being associated with an ALCAM-binding moiety, the therapeutic composition may be associated with a binding moiety that binds an adhesion molecule other than ALCAM, such as ICAM, VCAM, etc. In specific embodiments, a therapeutic moiety is associated with an ICAM-1 or JAM-1 binding entity. The ICAM-1 or JAM-1 binding entity may comprise part or all of MAC-1 and/or part or all of LFA-1, and it may comprise at least one ICAM-1 or JAM-1 minimal binding region. The binding site for the two β2 integrins LFA-1 and MAC-1 may comprise one or more of their I domains and/or one or more of a MIDAS motif, in specific cases. The MIDAS motifs bind to domain 1 at N terminus of ICAM-1.

In other cases, a therapeutic moiety is associated with a VCAM-1-binding moiety. The VCAM-1 binding moiety may comprise part or all of VLA-4, and it may comprise one or more VCAM-1 minimal binding regions. VLA-4 comprises a "leucine-aspartic acid-valine conserved (LDV) motif" that binds to domain 4 of VCAM-1, and a minimal binding region may comprise at least one of these domains.

In some cases, a therapeutic moiety is associated with an Addressin-binding moiety or a GLYCAM-1-binding moiety. The Addressin-binding moiety or a GLYCAM-1-binding moiety comprises part or all of Integrin alpha 4 beta 7 (LPAM-1), and it respectively may comprise one or more Addressin minimal binding regions or GLYCAM-1 minimal binding regions. LPAM-1 (alpha4/beta7) comprises tandem repeats of cysteine rich EGF like domains (essential for Ca++ binding), and one or more of these repeats may be included.

In specific embodiments, the therapeutic moiety can include Selectin binding domain, which may include lectin domain either in a monomer or a multimer form.

III. Examples of Methods of Use

Under normal conditions, immune-surveillance of the central nervous system (CNS) is very tight and few immune cells are able to cross the blood brain barrier (BBB). Trafficking of leukocytes from the bloodstream into pathological sites in the CNS is known to rely upon a complementary interaction of homing molecules acting in a concerted and specific manner. The dynamic pattern of homing molecule expression varies between normal and pathological conditions, with increased transmigration to the brain found in inflammatory and autoimmune diseases like multiple sclerosis (MS) but decreased trafficking in cancer. The differences in adhesion protein patterning between inflammatory and anergic endothelium and the molecules involved in this process are exploited to generate a novel platform to deliver cellular therapies to the brain, overcoming a critical barrier to improving human health.

Because cancer renders the endothelium anergic, abrogating T cell homing to brain tumors and hindering the development of effective cell therapy for CNS malignancies. Lessons learnt from infiltrative brain diseases can give insight into how to overcome the BBB block created by cancers. Activated Leukocyte Cell Adhesion Molecule (ALCAM; CD166) is a pathological adhesion molecule upregulated in the vascular endothelium of a number of infiltrative CNS diseases, such as MS, human immunodeficiency virus (HIV) encephalitis and experimental autoimmune encephalitis (EAE). Upregulation of ALCAM in these conditions further leads to overexpression of Intercellular Adhesion Molecule-1 (ICAM-1, CD54) and Vascular CAM-1 (VCAM-1; CD106), two ubiquitous adhesion molecules that mediate leukocyte BBB transmigration. Antibodies blocking ALCAM significantly decrease leukocyte access to the brain in EAE and HIV encephalitis, and antibodies to its cognate (heterophilic ligand, CD6) are currently being tested in a clinical trial for MS and graft vs. host disease (GvHD).

One can interrogate the mechanistic differences between the "anergic" brain tumor endothelium and the "facilitated" endothelium of infiltrative brain conditions. Surprisingly, it was found that ALCAM is highly expressed on glioblastoma (GBM) endothelium, while ICAM-1 and VCAM-1 are down regulated. Moreover, there was a significant induction of ALCAM associated with paradoxical downregulation of VCAM and ICAM expression when endothelial cells was cultured in supernatants from primary GBM cells or in TGFβ. GBM endothelium thus fails to launch the second wave of adhesion molecules necessary for effective BBB transmigration and, under the influence of tumor cells, eliminated baseline expression of second wave molecules.

The inventors mapped the ALCAM minimal binding region to domain 3 (D3) of CD6 (FIG. 5A) and generated an artificial molecule that serves as a novel cellular platform to reverse endothelial anergy. The exodomain of this molecule is comprised of D3 and a CD6 endodomain (-s), and one can express it on the surface of cells, such as T cells. D3-s T cells can crosslink to ALCAM on endothelial cells to increase T-cell adhesion and diapedesis through an ALCAM-overexpressing BBB model. One can characterize the ability of this system to induce T cell transmigration in mouse models of both GBM and inflammation. This paradigm-shifting line of research will not only enrich the understating of the T cell/endothelium interface, but will also enable the development of a broadly relevant cellular platform for targeted brain delivery of complex biologics. Such treatments are useful in particular for CNS diseases that are challenging to treat because of the sanctuary provided by the BBB that restricts both conventional and novel therapeutics. Generating a cellular platform for targeted brain delivery of complex biologics (CAR T cells, virus specific T cells, anti-inflammatory cells for autoimmune disease, oncolytic viruses and loco-regional vaccines or particulate matter such as nanoparticles, etc.) will therefore ensure adequate and targeted bioavailability of these drugs and minimizes the substantial risks of off-target toxicity.

Although any method of use may be employed for compositions of the disclosure, including ALCAM-binding moiety-comprising compositions, in specific embodiments the compositions are used for treatment or prevention of at least one medical condition. In particular cases there is a method of providing a therapeutic moiety to an individual using the compositions of the disclosure. In specific aspects, an individual that is provided an effective amount of one or more compositions encompassed by the disclosure is in need of therapy that targets desired particular cell(s) or tissue(s) comprising particular cell(s) in the individual. In at least some cases, the particular cells are ALCAM-expressing pathological endothelial cells, and such cells may or may not be present within the blood-brain barrier or beyond a vascular (endothelial) barrier.

In particular cases the ALCAM-binding moiety is expressed on a cell and cell-like platform, including any immune, somatic, hematopoietic, mesenchymal or stem cell, other blood cells such as red blood corpuscles and platelets. The ALCAM-binding moiety may also be used in secreted form or in a pharmaceutical preparation used to prime cells for targeted delivery. Examples of a cellular platform includes cells, such as immune cells (including CAR T cells, cytotoxic T cells, NK cells and NKT cells, among other immune effectors) or non-immune cells. Immune and/or stem cells (such as hematopoietic or mesenchymal stem cells) may be utilized for treatment of cancer, for example. Tregs or Th17 or other immune inhibitory cells may be delivered, such as for autoimmunity diseases, including multiple sclerosis or experimental autoimmune encephalomyelitis, for example. Cells may be delivered to counteract human immunodeficiency virus (HIV) encephalitis. Cells can be delivered for hypoxic or ischemic or infarctive conditions to improve the metabolism of the affected brain. Cells can be delivered to replenish a therapeutic molecules such as enzymes or hormone such as growth hormone or insulin. Corpuscles (non-nucleated cells such as red blood cells or platelets, including used as drug delivery systems), microsomes, miscelles, liposomes or other complex structures could also be used in this cell/cell-like platform.

In particular cases the ALCAM-binding moiety is expressed on a cell and cell-like platform to induce vascular occlusion of tumor microvasculature of malignant or other conditions and or delivery of therapeutic agents such as prostacyclins and other molecules to hypoxic, ischemic or infarctive areas of the brain or body.

In particular cases, the individual has a medical condition such as cancer (including at least brain cancer or metastatic cancers to brain (such as breast, lymphoma, etc.), EAE, MS, infection, meningitis, or CNS toxicity from idiopathic causes such as cytokine release syndrome, posterior fossa syndrome and others. The delivery of cells other than immune cells may occur, for example using mesemchymal stem cell for regeneration or drug delivery for Alzheimer's Diseases. Conditions such as MS, experimental autoimmune encephalomyelitis, pathogen infection, brain abscess, epilepsy, multiple sclerosis, Alzheimer's Disease, cerebral edema, cerebral ischemia, prion diseases, encephalitis, and inflammation may be treated. In cases wherein the individual has cancer, the cancer may or may not originate in epithelial tissues. In certain cases the individual is given an anti-infectious agent for a pathogen (virus, bacteria, or fungus, for example) using methods and compositions encompassed herein. Stroke may be treated with ALCAM-binding moieties of the disclosure, such as for delivery of prostaglandins, prostacyclines, vasoactive and metabolic agents, and agents affecting thrombosis, mesenchymal stem/stromal cells, or stem cells. In particular cases the compositions are used for brain or non-brain conditions wherein a unique endothelial signature can be targeted.

Embodiments of the disclosure provide for the ALCAM-binding moiety to be able to deliver cells or cell-like structures (for examples corpuscles, micelles, liposomes, etc.). Such a platform could deliver, in at least specific cases, one or more of the following: (1) a cell, as in CAR T cells, T reg cells, Th17 cells, and so forth; and/or (2) a therapeutic entity such as an engager, BiTE, scFv, replacement (enzyme or hormone). Such deliveries could be utilized for inflammatory, malignant, infectious, autoimmune or vascular/hypoxic conditions, as examples.

Methods of the present disclosure target delivery of one or more biologics (large, complex molecules or mixtures of molecules) or simpler molecules or agents to an individual, including to a particular tissue of an individual in at least some cases. In certain cases, an ALCAM-binding moiety, or multiples thereof, are operably linked to other domains, including to a therapeutic, that may facilitate targeting of the therapeutic to a particular tissue or may facilitate other aspects of the therapeutic. For example, in specific cases the ALCAM-binding moiety is expressed as part of a molecule on a cell and that cell may be an immune cell that itself has therapeutic properties for a medical or condition in need of treatment or for research. In some cases, the cell has one or more other engineered molecules expressed thereby.

Methods of the present disclosure also utilize successful homing of cells to their targets by targeting cells or tissues that express ALCAM or other adhesion molecules. In at least some cases, by targeting ALCAM a therapeutic moiety is homed to its target, for example by breaching an endothelial/epithelial barrier and/or the BBB.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A Cellular Platform for Targeted Delivery of Complex Biologics

Embodiments of the present disclosure establish a cellular platform for enhanced targeted delivery of therapeutic complex biologics to pathological sites. In specific embodiments, an ALCAM minimal binding element MBE ("CD6 and stalk") expression on immune cells enhances ALCAM-specific targeted delivery of therapeutic complex biologics to pathological sites, including across the blood-brain barrier (BBB).

Validation of the Expression of ALCAM.

ALCAM Expression in Glioblastoma (GBM) Endothelium.

Three random GBM paraffin blocks were sectioned at 5 μm thickness and immunohistochemically stained against ALCAM CD166 using mAb. The 3 samples stained positively for ALCAM in the GBM stroma (around the vessels lumen) and in the core tumor cells. Also, immunofluorescence staining of cryosection slides with CD31+ and ALCAM; affirm the clear localization of ALCAM in the CD31+ vessels (colocalized signal of CD31/ALCAM signal). Recent literature highlighted the role of CD166 in tumor invasion and in recruiting T-regs to the tumor site. Hence, ALCAM Thus, ALCAM is key adhesion molecule in cancer pathological endothelium and its induction in the tumor endothelium plays a role in cancer metastasis or immune cells trafficking.

Fresh GBM endothelium was isolated from GBM surgical excision samples. Characterization of the primary endothelium with three different pan endothelial markers: CD31, Von Willebrand Factor (vWF), and VE-Cadherin, is shown in FIGS. 1A and 1B. Intriguingly, ALCAM was upregulated at basal level in comparison to normal brain endothelium. Cells stained by flow cytometry were double positive for ALCAM and CD31 (FIG. 2). In immunofluorescence ALCAM and C31 colocalized in tumorogenic vascular wall. Additionally, ALCAM expression was further enhanced with TNFα, Hypoxia and upon incubation of normal endothelial cells in GBM cell culture supernatant or in TGF beta.

ALCAM Expression in Pathological Endothelium.

To validate ALCAM as a homing target upregulated on endothelium during pathological conditions, FACS analysis was performed for ALCAM expression in 3 pathological conditions: inflammation (blue open histogram), hypoxia (black open histogram) and tumor supernatant (red histogram). Six endothelial cell lines were stained, (3 murine: BALB/c Mouse Primary Brain Microvascular Endothelial Cells from Cell Biologics, bEND.3, 2H-11) and 3 human cell lines were stained: lry GBM tumor endothelium, HBMEC, HUVEC). The inventors compared ALCAM staining pattern to basal expression (dotted blue histogram); negative control IgG1-PE isotype shown in grey filled histogram. ALCAM was significantly overexpressed in all condition compared to minimal expression under physiological conditions (FIG. 3).

Figure 4:
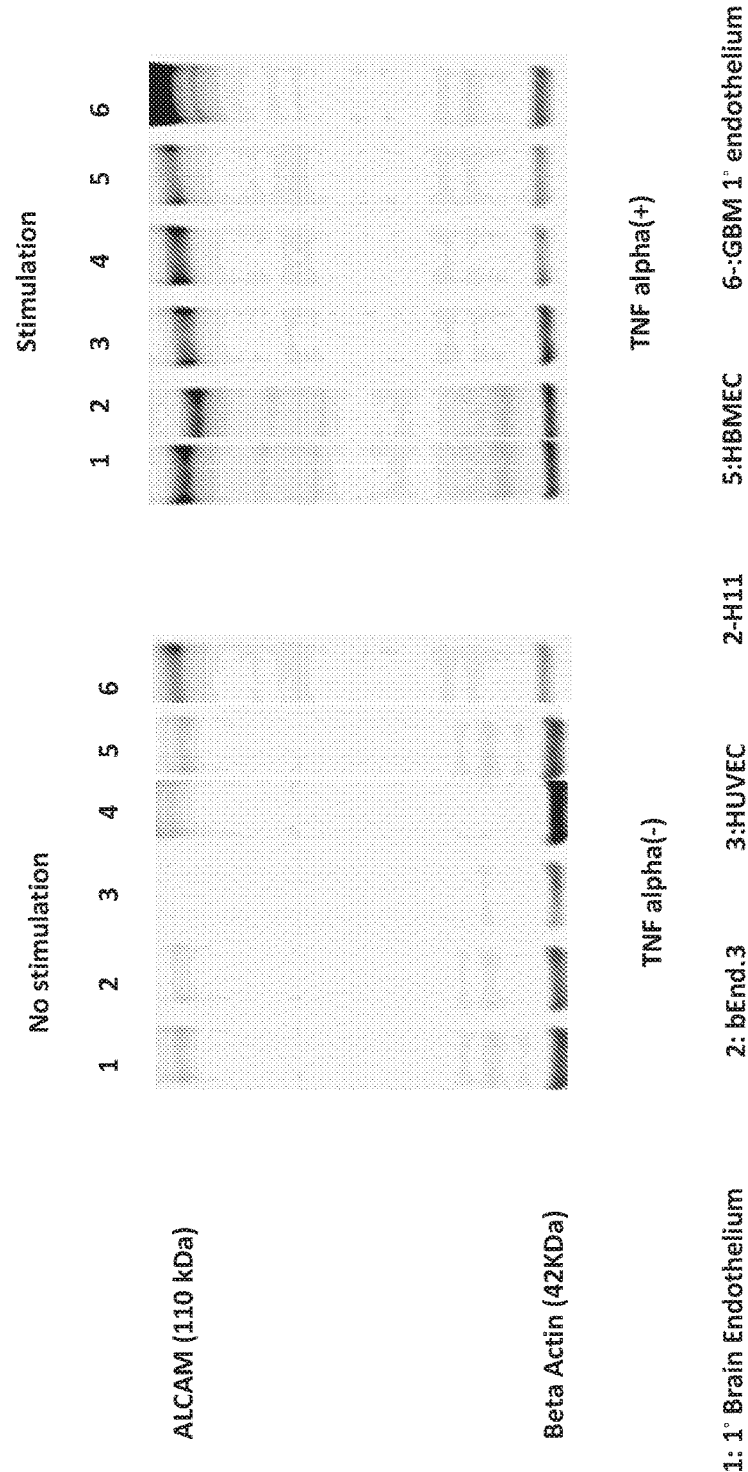
FIG. 4 is a Western blot analysis of 10 μg protein to probe with ALCAM mA over a battery of endothelial cell lines.

To confirm the results, the inventors membrane fractionated 6 endothelial cell lines using sucrose gradient and used Western blot analysis of 10 ug protein to probe with ALCAM mAb (FIG. 4).

Engineering a Ligand to Specifically Bind ALCAM

Design of ALCAM Binding Constructs.

Considering the X-ray crystallography for the 3D structure of ALCAM and CD6, the inventors designed and constructed artificial ALCAM ligands comprised of an exodomain and an endodomain joined via a transmembrane domain (TM). The exodomain comprised ALCAM minimal binding domain (MBE) that comprises CD6 Domain 3 and its Stalk. Exodomains were designed consisting of a MBE monomer, trimer and pentamer. The wildtype CD6 TM domain joined the endodomain to either a wildtype CD6 intracellular signaling domain or a truncated/mutated wildtype CD6 intracellular signaling domain. (FIG. 5B)

TABLE 1

| | | |
|---|---|---|
| Monomer 1xD3 CD6 truncated/mutated (1-D3Δ) | Trimer 3xD3 CD6 truncated/mutated (3-D3Δ) | Pentamer 5xD3 CD6 truncated/mutated (5-D3Δ) |
| Monomer 1xD3 CD6 with signalling domain(1-D3) | Trimer 3xD3 CD6 with signalling domain(3-D3) | Pentamer 5xD3 CD6 with signalling domain (5-D3) |

Detection of ALCAM Binding Constructs.

Three main methods were used to confirm the transduction and the surface expression of the artificial (MBE) CD6 D3 receptor.

Data shown are for monomer, trimer and pentamer-transduced T cells:

A) FACS analysis was used to confirm ALCAM specific binding to MBE CD6 D3 constructs on the surface of primary T cells. Cells were incubated with IgG1 Fc linked recombinant human ALCAM followed by an anti-human IgG1 Fc FITC conjugated Ab (filled black histogram). Staining of cells with anti-human IgG1 Fc FITC alone (open grey histogram), staining of non-transduced T cells (NT) (dotted open histogram) served as control for basal CD6 expression on normal T cells which bind natively to ALCAM.Fc. and percentage transduction is determined after staining of monomer, monomer+signaling domain, trimer, trimer+signaling domain, pentamer and pentamer+signaling domain (grey-filled histogram) (FIG. 6).

B) FACS analysis using a specific mAb for domain 3 of CD6 (a kind gift from Dr Brown, Oxford university) was performed. Cells were incubated with primary mouse Anti-human CD6 domain 3 antibody followed by a 2ndry PE conjugated Goat polyclonal to anti mouse IgGAb (blue-filled histogram). Staining of cells with anti-human IgG1 FITC alone (open grey histogram), staining of non-transduced T cells (NT; dotted open histogram) served as control for basal CD6 expression on normal T cells (FIG. 7).

C) FACS analysis using a specific mAb for 6× His TAG. Cells were incubated with primary mouse 6× his mAb conjugated to PE (filled red histogram). Control staining of cells with anti-human IgG1 FITC alone (open grey histogram), and staining of non-transduced T cells (NT) (dotted open histogram) (FIG. 8).

Functional Testing of Engineered Cells Overexpressing [MBD]"

Dissecting the Effect of the Engineered Molecules on the Extravasation Multistep Cascade of the T Cells (Rolling, Adhesion, Transmigration).

Collectively, the data presented herein point to the fact that T cells transduced with "ALCAM minimal binding domain" have enhanced molecular interactions with ALCAM-expressing pathological endothelial cells.

1) Dynamic Cell Adhesion and Rolling in Microfluidic Chamber "Bioflux System"

Methods:

The Bioflux System is a 24-well Plate with 8 independent experimental channels (two inputs per channel). Movies of cell rolling are captured with an exposure time of 100 ms at 500 ms intervals. A stack of thirty consecutive images were captured 0.5 seconds apart (100 ms exposure). Endothelial cells were seeded over fibronectin pre-coated BioFlux™ channels. After reaching a monolayer confluence, ALCAM stimulation with TNFα and IFNγ were done for 6 hours. Control non-transduced vs T cells were injected to the system simultaneously. Adhesion and rolling were assessed under flow with a shear of 2 dyne/cm$^2$. Stationary cells were counted in 10 fields of view then the average value was calculated. Also for rolling velocity, 100 frames/sec time-lapse frames were taken and analyzed using ImageJ® software. T cell tracking allowed to calculate the distance travelled, hence maximum, minimum and mean velocities/sec were calculated. Three independent experiments were done.

Summary of Results:

First: Increased Adhesion of [MBE]$''$ T Cells Over Multiple Endothelial Cell Lines.

Figure 9:
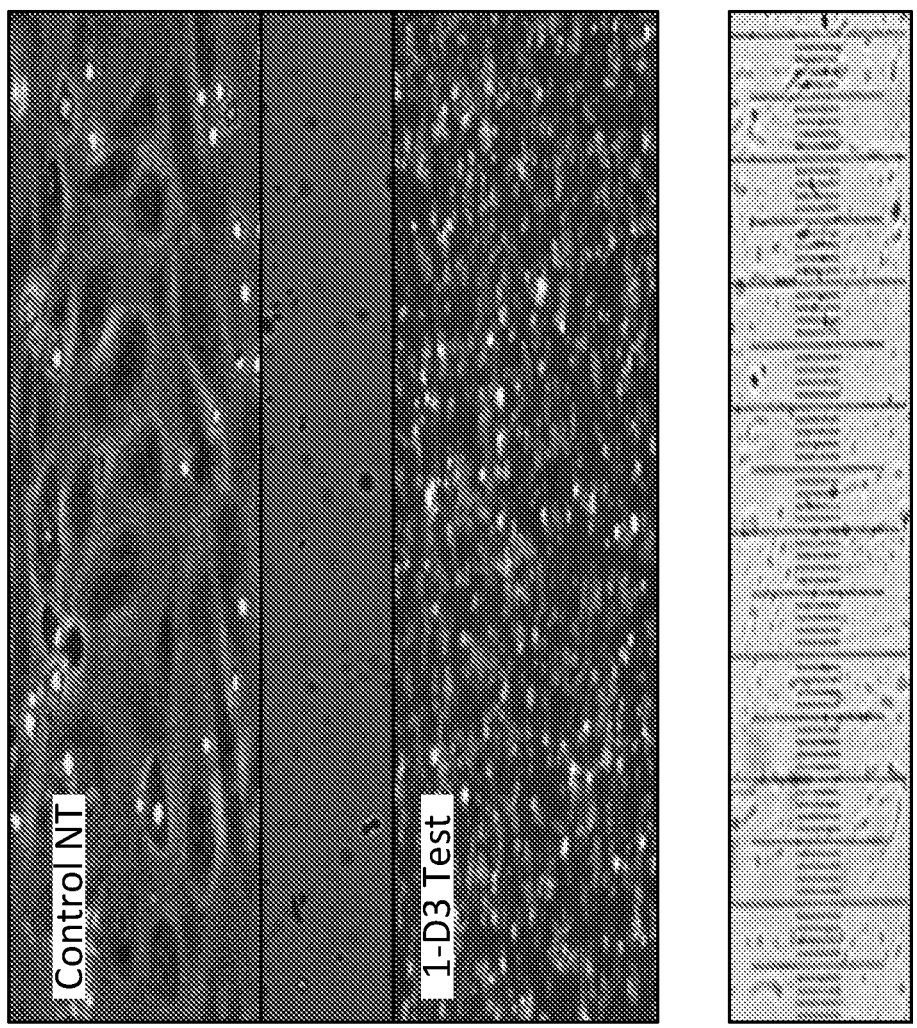
FIG. 9 is a snap shot of the Bioflux fluidic chamber (simultaneous two channel view; upper NT and lower Test cells expressing MBE receptor). This field of view shows that [MBE]″ T cells reached roll with slower velocity until reaching a fast arrest over ALCAM+ endothelium in comparison to normal non-transduced T cells.

Faster adhesion of [MBE]$''$ T cells under shear force 2 dyne/cm$^2$ was significant in all transduced cells vs the non-transduced controls and higher firm arrest percentage over ALCAM+positive endothelium (FIG. 9).

Second: The Rolling Velocities of [MBE]$''$ T Cells were Significantly Lower than Normal Non Transduced T Cells.

Figure 11:
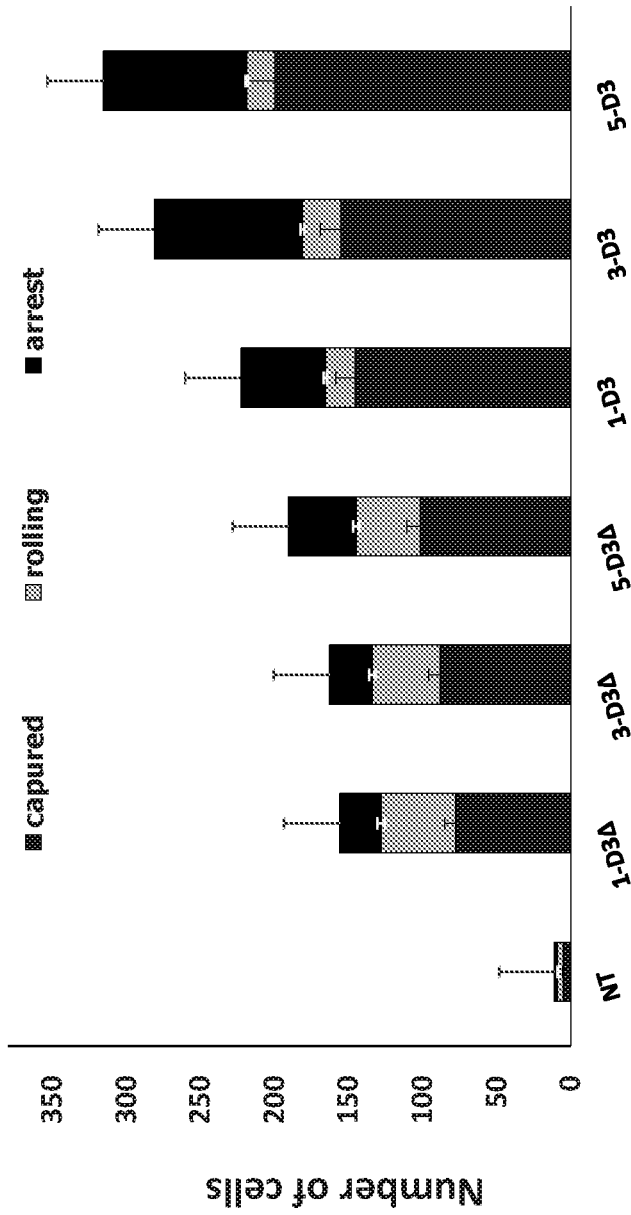
FIG. 11 is a bar graph showing the dynamic behavior of transendothelial migration under flow. It compares the number of cell captured, rolling; and finally arrested over the endothelium monolayer. MBE T cells showed better Transendothelial steps (adhesion, tethering and rolling) that precede extravasation into the tissues.

Under normal shear conditions (2 dyne/cm$^2$). All [MBE]$''$ significantly roll slower than the NT control cells. Moreover, the [MBE]$''$ T cells with truncated D3 were able was able to roll in a slower velocity for longer time while [MBE]$''$ T cells with signaling domain roll slower for shorter time yet tightly adhere to the endothelium. (FIGS. 10 and 11).

Third: [MBE]$''$ T Cells Reached a Faster Arrest.

Figure 12:
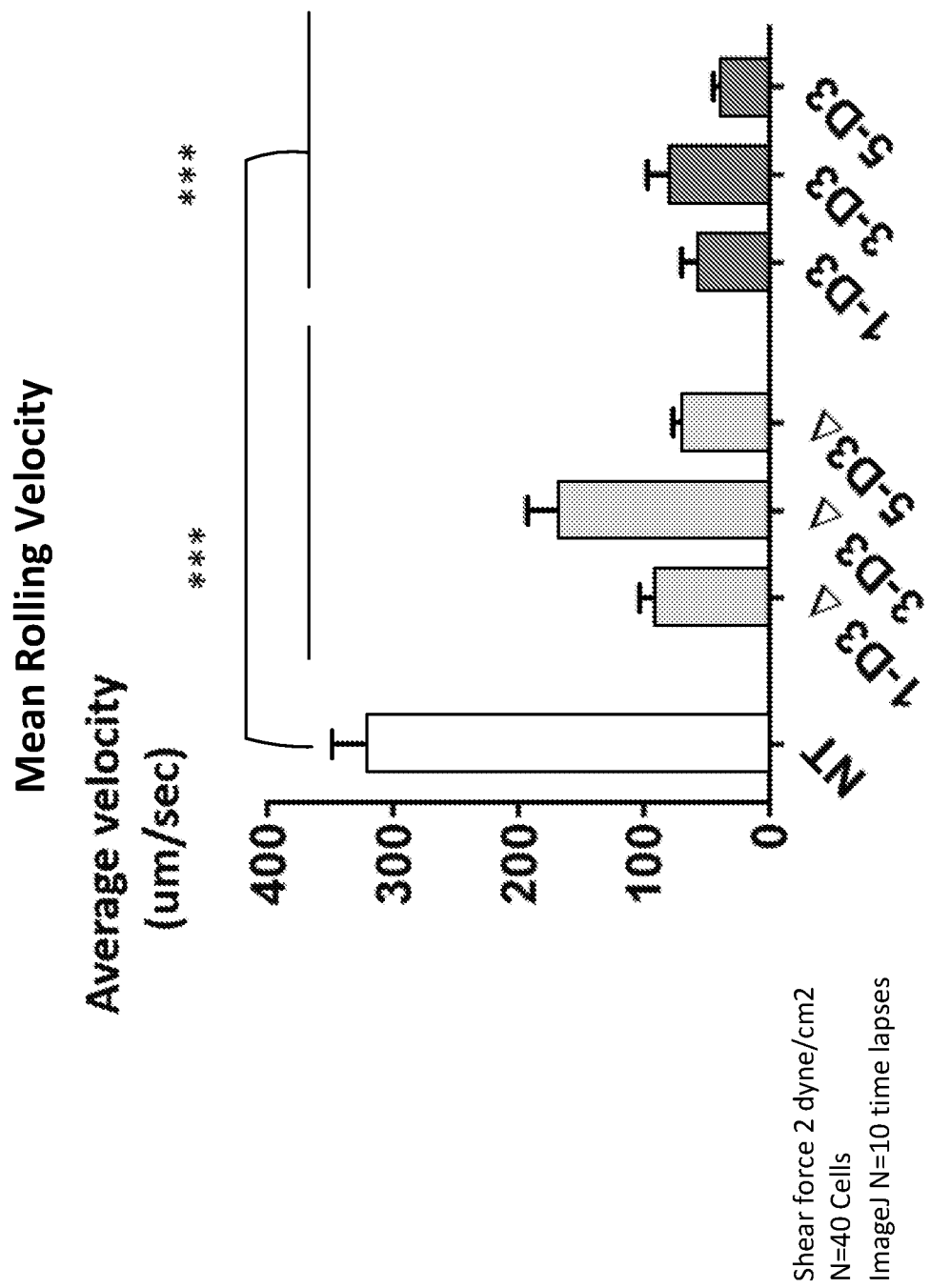
FIG. 12 is a bar chart that represents mean velocity in μm/sec. The graph is showing MBE T cells roll slowly over endothelium; which allow them to efficiently to tether and transmigrate through the endothelium monolayer. Transduced MBE T cells simultaneously with Non-transduced control T cells were injected to Bioflux channels at a density of 1×10⁶ cells/ml in test media. Shear was adjusted during the experiment from 3 to 1 dyne/cm² using the BioFlux 200 controller. Movies of cell adhesion and rolling were captured with an exposure time of 100 ms at 500 ms intervals (A stack of thirty consecutive images were captured 0.5 seconds apart (100 ms exposure). Fraction of rolling cells were counted per field of view (n=10) and Velocity calculation were done using Mjtracker in ImageJ software. Data were analyzed by two-way ANOVA and Tukey's post hoc test; three repeated experiments were done in the VA lab in BCM. Error bars are STEV; * P<0.05, P<0.01, *P<0.001. All MBE cells has significant lower velocity in comparison to Control Non transduced cells.
Figure 13:
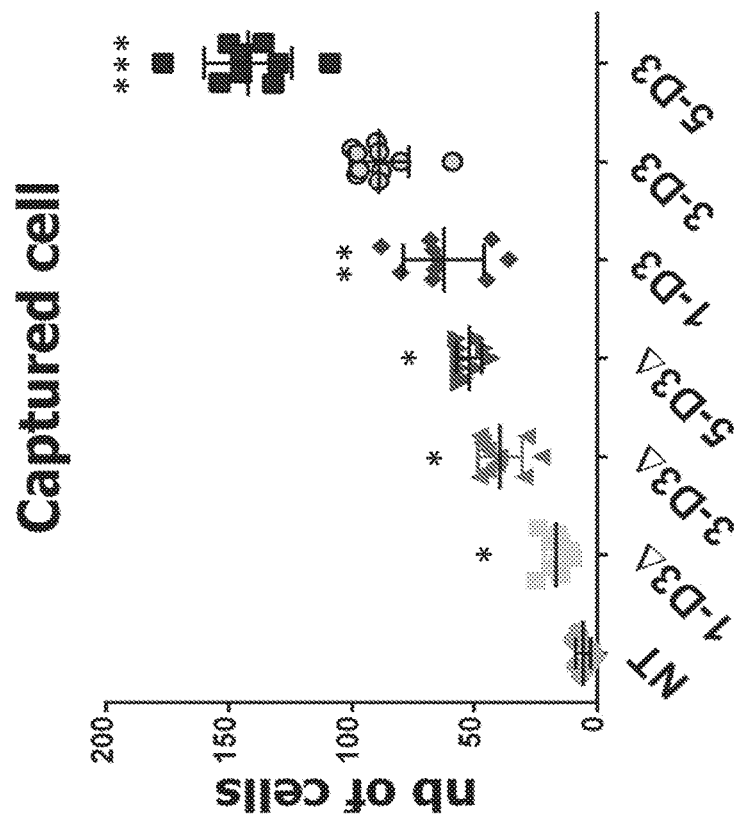
FIG. 13 is an assessment of the arrest of [MBE]ⁿ T cells/10 field T cells over endothelium. The Capture step under shear force (2 Dyne/cm²) is essential for MBET cells to initiate the TEM process over ALCAM+ endothelium preceding the homing to their targets. [MBE]ⁿ multimerization increases the adhesion ability to ALCAM+ cells (5D3>3D3>1D3)

This, coupled with the first observation (the relative increase of static adherent cells over the endothelium monolayer over time), indicated a firmer adhesion of [MBE]$''$ T cells (FIGS. 12 and 13).

2) Transmigration Using Boyden Chamber Assay

Methods:

T cell transmigration across the endothelium co-cultured with inverted astrocyte to mimic the BBB was assessed in all cells transduced with [MBE]$''$ constructs and compared to non-transduced controls. A static two chamber transwell platform was used where an upper chamber is seeded with monolayer of endothelial cells stimulated with TNFα and coated with astrocytes on the bottom to mimic the endothelium/pericytes barrier. The lower chamber is filled with GBM supernatant to attract T cells. T cells are added on the upper chamber and left for 24 hours, collected transmigrated cells in the down well, stained with WST-1 dye, then the measurement of the Optical density at 499 are directly correlating with percent of migrated cells through the artificial BBB.

Figure 14:
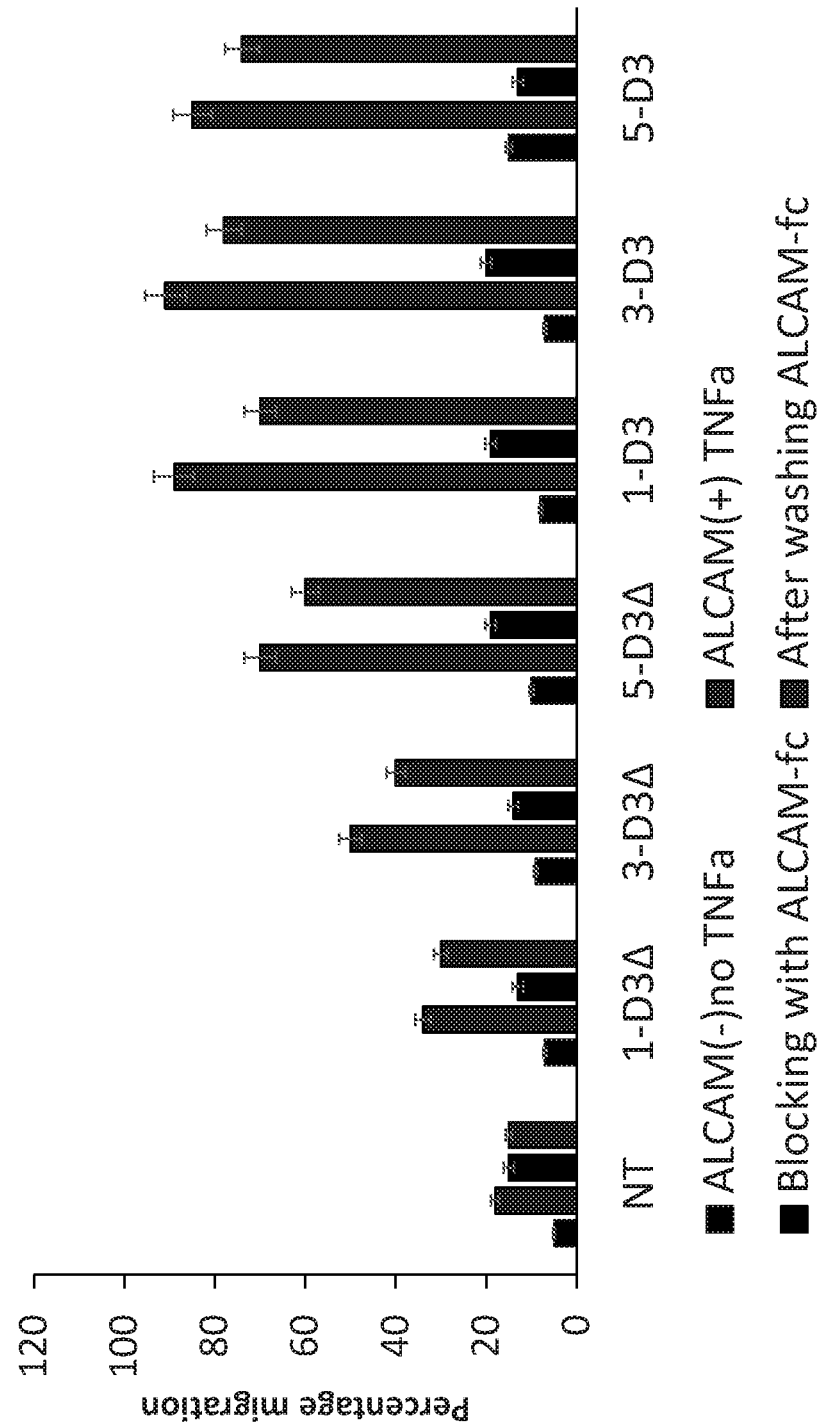
FIG. 14 shows transmigration advantage of [MBE]ⁿ T cells across endothelium/pericytes barrier, and this model simulates the vascular arrangement as well as the blood brain barrier; MBE T cells showed significant higher tranendothelial migration percentage conditional on ALCAM presence. In a transwell assay, 1×106 cells were seeded over the upper chamber (pre-coated with endothelial monolayer and inverted Atrocytes). Cells are allow to migrate for 24 hours then collected from the lower chamber and quantified calorimetrically using WST-1 reagent. Data were analyzed by two-way ANOVA and Tukey's post hoc test; three repeated. Error bars are STEV; * P<0.05, P<0.01, *P<0.001.

Summary of Results:

The degree of transmigration was directly proportionate to the multimerization of MBE (D3) and more enhanced reaching saturation depending on the presence of the signaling domain. (FIG. 14). The truncated pentamer showed higher migration ability than the trimer. Then trimer showed higher migration than the truncated monomer. (5-D3Δ>3-D3Δ>1-D3Δ). while [MBE]$''$ T cells with signaling domain had higher transmigration activity comparing to the truncated ones. The latter phenomena is related to signaling domain contribution in priming T cells through the inside out activation of LFA-1 to higher adhesive and invasive state. (FIG. 19-33)

In order to exclude the proliferation effect mediated by the signaling domain of the cells after transmigrating in the lower chamber, flow cytometry eFluor 670-proliferation experiment was done for all [MBE]$''$ T cells with various CD6 constructs, the results showed that all the transduced cells had insignificant proliferation compared to the non-transduced control. Moreover, the same transwell experiment was repeated with irradiated cells (incapable of proliferation), and the transmigration pattern was preserved.

In order to confirm that the fold increase of migration seen is specifically related to ALCAM-CD6 D3 interaction, the inventors employed blocking ALCAM-fc over T Cells and endothelium. After blocking, significant decrease in the transmigration pattern was observed. This effect decreased while after washing the blocking agent (with 10% BSA complete media over 4 hours shaking) and the transmigration across the endothelium is restored. (FIG. 14)

Collectively, this assay highlighted the differential enhanced migration pattern of all [MBE]$''$ (CD6 D3) engineered T cells compared to normal T cells. Hence, the transmigration of T cells employs ALCAM-CD6 specific interaction.

Impedance Based Assessment of Migration of Various of [MBE]n T Cells

Figure 15:
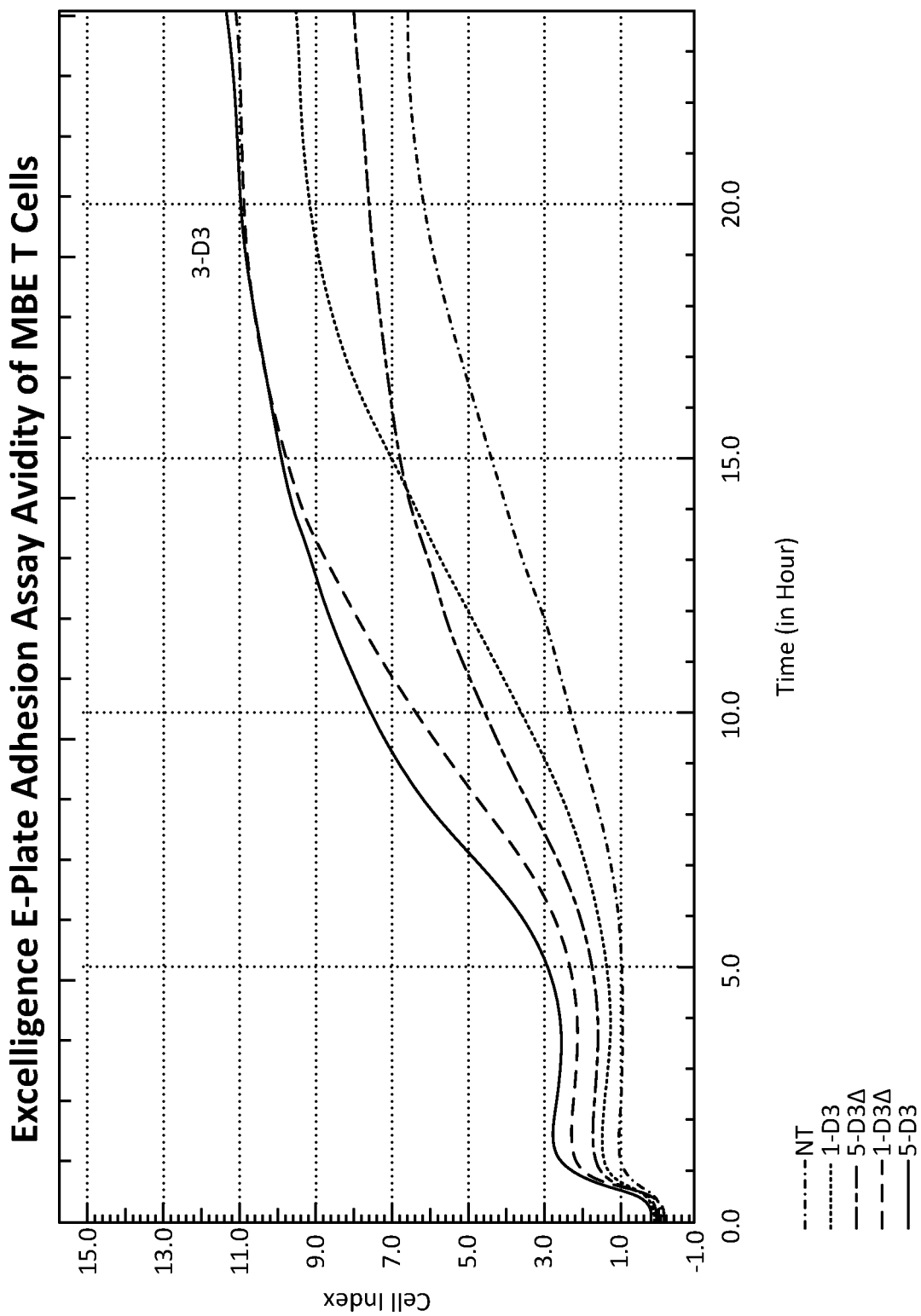
FIG. 15 shows an adhesion assay using of the xCELLigence impedance system to assess the adhesion avidity of the different multimer of MBE on ALCAM positive surface. The E-plates were coated with 1 μg/ml ALCAM-fc and then different [MBE]ⁿ T cells were added to assess the adhesion through the increase in cell index with time.

The xCELLigence impedance system was used to assess, in depth, the migration pattern of [MBE]$''$ T cells over a prolonged time period. Adhesion over ALCAM-Fc coated plate (10 ng/ul), cell index increase with increase cell attached to ALCAM (NT green<monomer truncated<pentamer truncated<monomer with signaling domain<pentamer with signaling domain) (FIG. 15).

Figure 16:
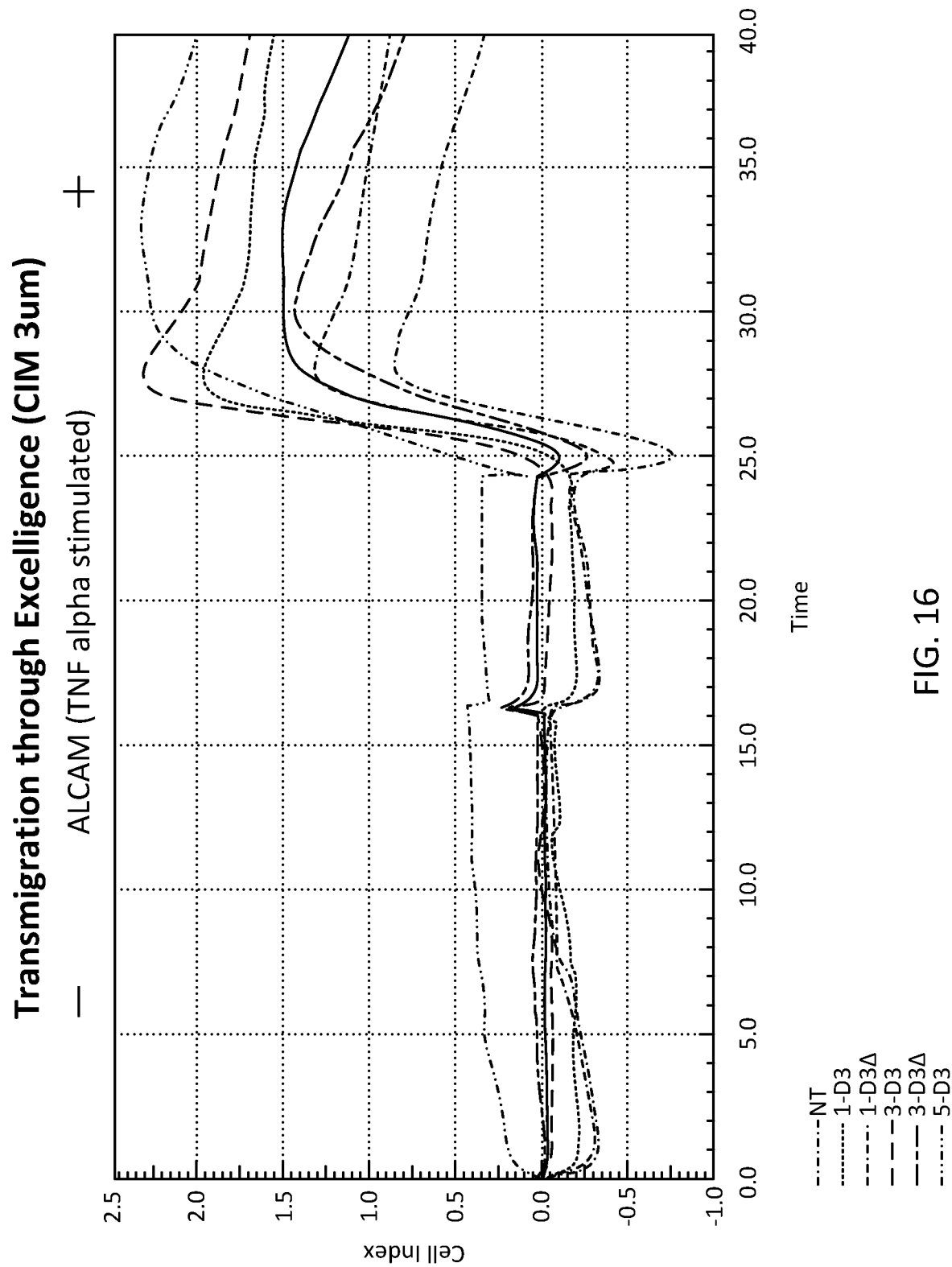
FIG. 16 is a migration assay using the xCELLigence CIM plates to assess the dynamic migration pattern of [MBE]ⁿ T cells over a prolonged time period. CIM paltes have the electrode the lower chamber tin order to detect the migrated cells only. [MBE]ⁿ T cells shows higher migration pattern through CIM exclligence plate. 1×10⁶ cells/ml are seeded over the upper chamber of the CIM plate and the impedence is detected if the cells transmigrate to the lower wells where the Gold electrodes are present.

Transmigration across CIM transwell plate coated with endothelial cells was assayed. Minimal migration was detected over ALCAM negative-endothelium with no TNF alpha stimulation while significantly higher transmigration with increased cell index over 24 hour with ALCAM positive+ endothelium (with TNFα) (monomer truncated<Trimer truncated<pentamer truncated<monomer with signaling domain<trimer with signaling domain<pentamer with signaling domain) (FIG. 16).

Demonstration, at the Molecular Level, the Interaction Between ALCAM and [MBE]n Using Proximity Ligation Assay (PLA)

Methods:

The principle of the technology is based on two unique probes provided with the Duolink kit. Each PLA probe (+ and −) consists of specific mAb to a target protein and it is attached to a unique synthetic oligonucleotide, which acts as a reporter. When proteins interact closely, the probes are at a critical proximity allowing for a DNA bridge to hybridize. The bridge is then amplified and a fluorescent signal is produced. The distance of the oligonucleotides, which allows DNA hybridization and ligation has to be <40 nm).

Figure 17:
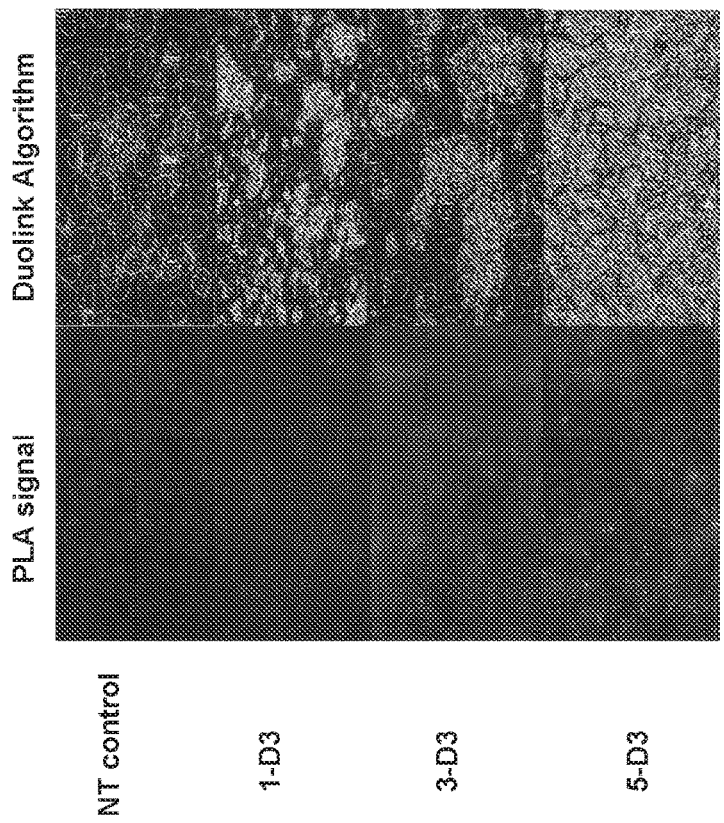
FIG. 17 shows the Proximal ligation assay of ALCAM/(MBE) D3 that demonstrates [MBD]ⁿ T cell form podosynapse with ALCAM (<40 nm interaction) over the pathological endothelium to initiate the transmigratory cup formation mediating efficient migration of the cells to their targets. Fluorescent Microscopic Imaging of Duolink Proximity Ligation Assay Detecting D3 on T cell and ALCAM positive targets Interactions. A monolayer of tumor endothelial or (ALCAM+HBMEC cells (pre-induced with TNF alpha 1 0 μM) were co-incubated with 1-D3 T cells, 3-D3 T cells, 5-D3 T cells and NT T cells, respectively in 8 well chamber slide. They were mounted and fixed, and the Duolink Proximity Ligation Assay was performed to detect (within 40 nm) co-localization of ALCAM and D3 at the transmigratory (pseudo-synapse between T cells and endothelial cells). Images were captured with fluorescent confocal microscopy. PLA signals were detected (<40 nm) using Duolink ImageTool. Positive signal is indicated by red fluorescence. The total PLA signal per region of contact was significantly higher in the D3 engineered T cells in comparison to control NT and respectively increased with D3 multimerization.
Figure 18:
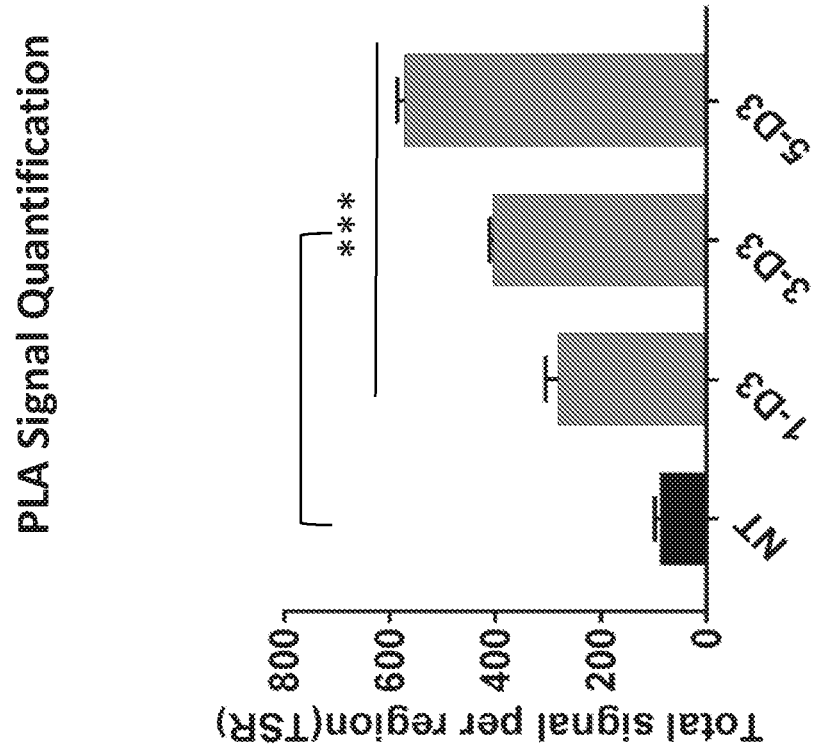
FIG. 18 provides a bar graph showing proximity ligation assay (PLA) total signal per cell (TSC); Objective quantification of proximal ligation assay (PLA) signals (<40 nm) using Duolink ImageTool. Bar chart shows total number of PLA signals per region of contact between T cells and AlCAM+ cells (TSR). TSR was directly proportional to number of CD6 "D3" and ALCAM molecular interaction; 5-D3>3-D3>1-D3. Data were analyzed by one-way ANOVA and Tukey's post hoc test; n=83-103 cells from three experiments. Error bars are STEV.; P<0.01, *P<0.001.

For a purpose, mAb against ALCAM was linked to a direct probe (−) and CD6 D3 specific mAb was linked to probe (+). PLA was done in a chamber slide where T cells are fixed over a monolayer of endothelial cells. Every condition was tested in separate multiplicates and the negative control was included using one probe only. Red fluorescent signal was analyzed using the DuoLINK software analysis (see FIGS. 17 and 18).

Investigating the Role of the CD6 Signalling Domain for T Cell Transmigration:

CD6 intracellular domain is associated with multiple signaling networks inside T cells in order to achieve high integrin activation and eventually better transmigration.

Figure 19A:
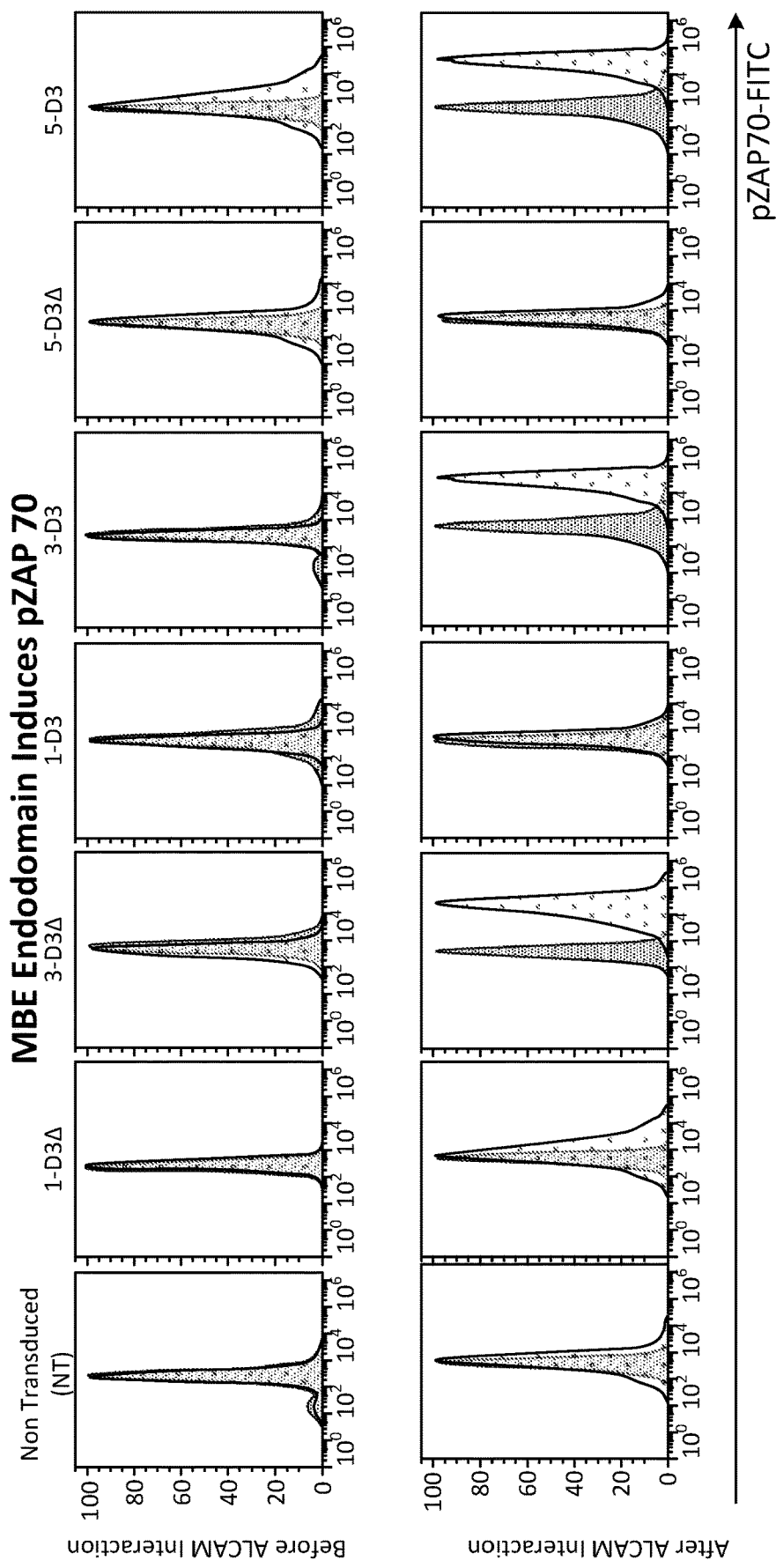
FIG. 19 demonstrates differential expression of pZAp-70 before and after transmigration. 1×10⁶ cells are fixed and permeabilized, then stained for pZAP-70 PE.
Figure 19B:
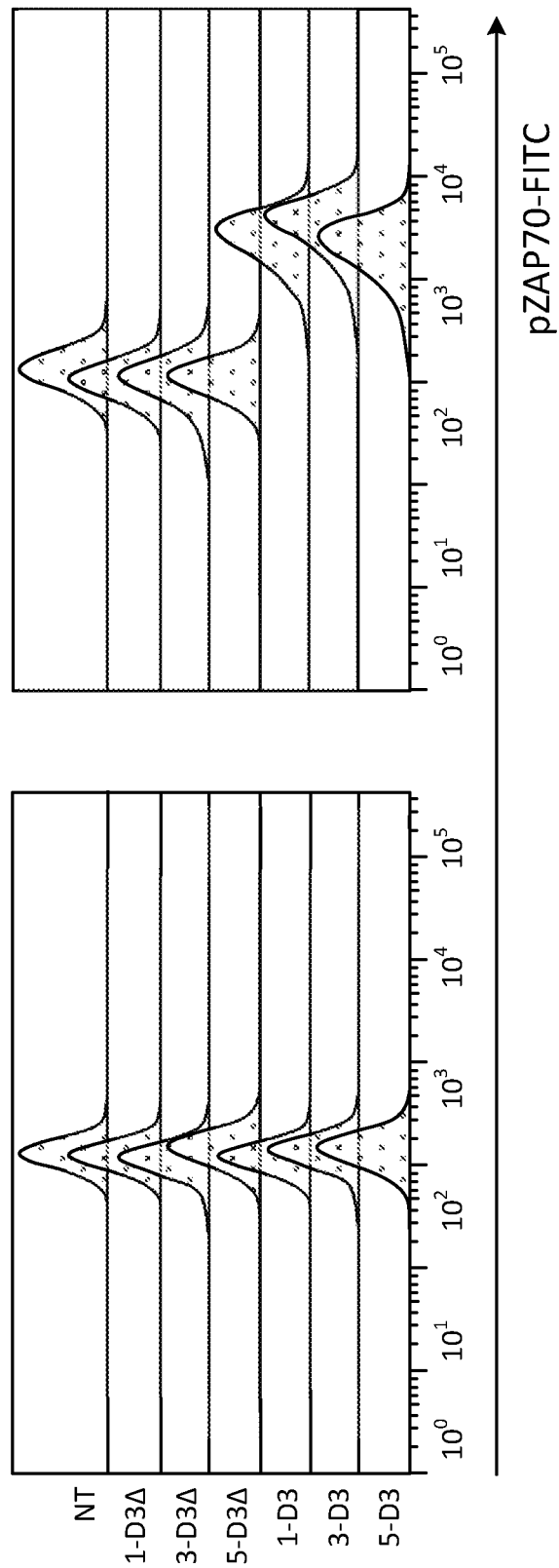

ZAP-70 Signalling:

Methods:

The cells were fixed in 4% paraformaldehyde and permeabilized with 0.5% tween, then incubated with 7 uL pZAP-70-FITC (7 mg/mL) for 30 mins on ice. Staining with IgG1-FITC isotype shown in black line. Differential expression of pZAP-70 before and after transmigration shown in red lines. There was a shift in PZAP-70 detected in all cells migrated but the only remarcable shift in pZAP-70 was detected in T cells bearing a signal domain which suggest that ALCAM-CD6 interaction fires intracellular signal cascade that involved phosphorylation of ZAP-70 (key signal mediator in T cells) (FIG. 19).

Figure 20A:
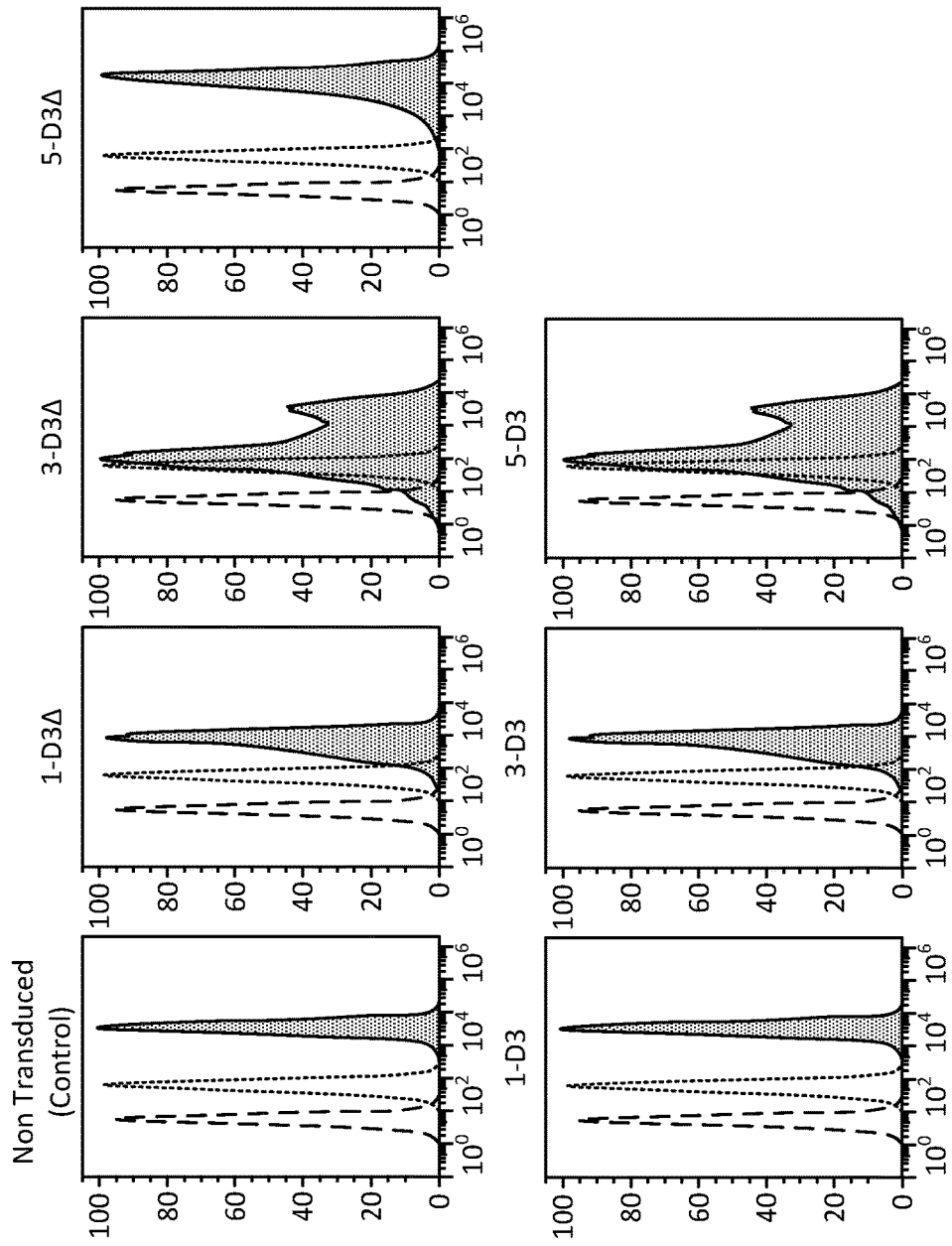
FIG. 20 shows that Talin expression was upregulated in migrated cells and enhanced with the transduced T cell with monomer D3 and pentamer D3 bearing the intracellular CD6 signaling domain.
Figure 20B:
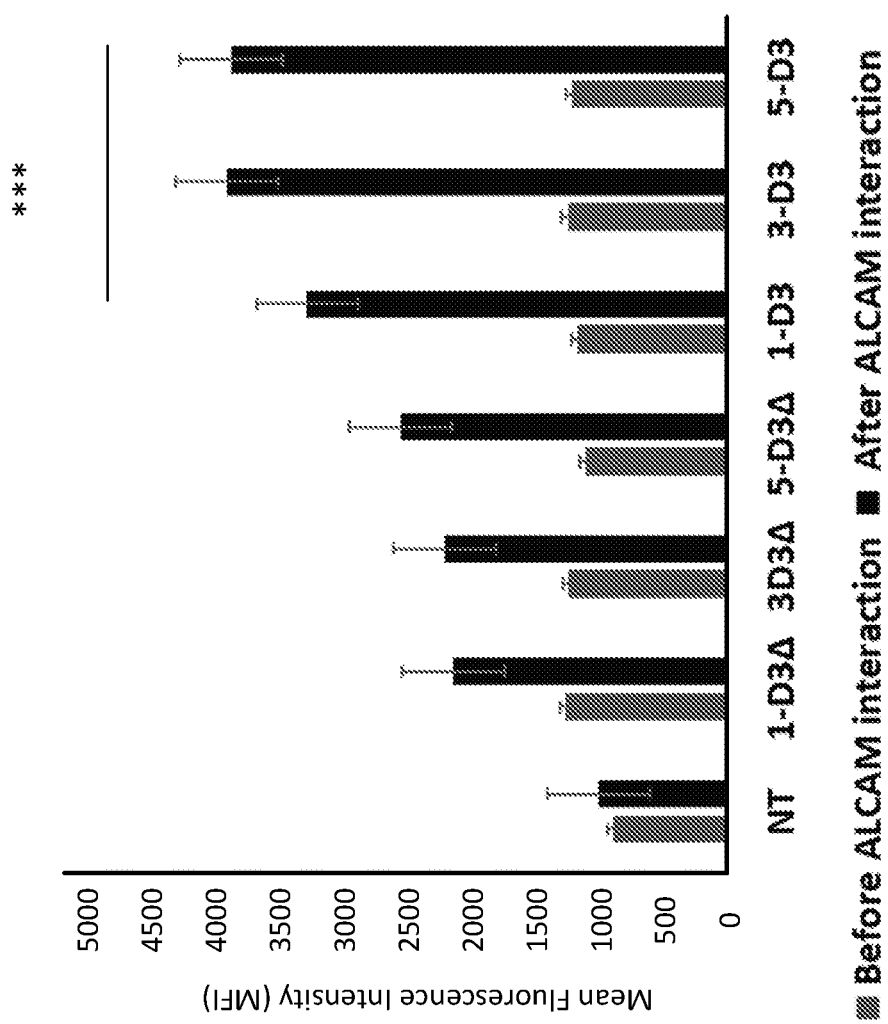

Talin Expression Mediated by Zap-70:

Methods:

Intracellular staining with Talin—primary antibody (3 mg/ml) for 30 mins. The cells were then incubated with 2ndry PE conjugated Goat polyclonal to anti-rabbit IgG. Negative control staining (grey line) with Goat polyclonal Anti-Rabbit IgG was done and staining for Talin-1 in T cells before transmigration showed in Blue line and after (post ALCAM-CD6 interaction) showed in Red line. Talin expression was upregulated in migrated cells and enhanced with the transduced T cell with monomer D3 and Pentamer D3 bearing the intracellular CD6 signaling domain. These results coincides with the literature pointing to the role of zap-70 and Talin in integrin open confirmation and easing the migration operation. The cells were then incubated with 3 μl primary antibody (3 mg/ml) for 30 mins. The cells were then incubated with 2ndry PE conjugated Goat polyclonal to anti-rabbit IgG. Enhanced expression of Talin-1 was notable in T cells engineered with CD6 signaling domain (FIG. 20)

LFA-1 Inside Out Activation is Mediated by Talin Upregulation.

LFA-1 is ubiquitous adhesion molecule needed for priming the cells to the adhesive state prior to the migration step. (FIG. 32).

Methods:

LFA-1 extension or opening of the beta domain, critical for high-affinity LFA-1, detected by the reporter mAbs KIM127. T lymphocytes were fixed with 4% parafolmadehyde; then incubated with the biotin-labeled KIM127 mAbs (10 mg/ml) before and After ALCAM binding for one hours. Then the cells were then incubated with 2ndry antibody conjugated streptavidin labeled with Alexa Fluor 568-. Blue histogram denotes LFA-1 extended confirmation before ALCAM interaction and red histogram denotes LFA-1 open confirmation after ALCAM interaction A, respectively, and black lines denote background staining by a secondary only streptavidin Alexa-568.

Actin/Focal Adhesion Induction at the D3/ALCAM Interface Mediating the Stability of the Migrating Cells was Assayed.

Methods:

Super resolution imaging at 40× and 60× of the cells on ALCAM+ surface. Cells were fixed in 4% parafoladehyde then permealized with ice cold methanol; then stained with FAK 1ry antibody followed by secondary ALexa fluor 488, the incubated with Phalloindin Texas Red, then DAPI nuclear staining.

FIG. 33A-33E staining of F-Actin/focal adhesion Kinase (FAK) that are essential for the cytoskeleton organization of the migrating cells and mediate efficient invasion capacity over ALCAM+ endothelium. FIG. 33A shows the colocalization of F-actin and FAK in MBE cells in comparaison to control cells. FIG. 33B shows Total internal Reflection fluorescence TIRF imaging at 60× where the high resolution of F-actin induction at D3/ALCAM interface is significantly detected. FIG. 33C quantification MFI-Actin on the cell surface using FIJI software, F-actin intensity n MBE cells is highly significant in comparison to NT T cells. FIG D represents the Structural illuminating Microscopy SIM at 60× image of MBE T cells after ALCAM interaction. It shows the invadopodia and the actin raffle with the focal adhesions that mediate T cells endothelial invasion. FIG E/F show TIRF imaging at 60× of the stretch induced Focal adhesion Kinases (FAK). MBE T cells has higher FAK intensity that enable them to protrude and invade the endothelial/epithelial Barrier In Vivo: Accessing CD6 Transduced T Cells Homing Efficacy to Pathological Site Bioluminescence T Cell Tracking:

Accessing homing of T cells with different CD6 constructs to an orthotopic Brain tumor model in SCID mice. T cells were double transduced with GFP-FFLuc in order to be tracked with bioluminescence in vivo.

Methods:

Mice were injected with 50,000 U373-GBM or Daoy tumor cells, 10×10$_6$ T cells were injected IV, then using BLI, the inventors assessed the differential trafficking to the brain tumor over a period of 0 days between control non-transduced group and transduced test group. Preliminary data showed that T cells overexpressing the CD6 D3 monomer truncated construct home better to the brain tumor.

T Cell Infiltration to the Tumor Explants:

Assessing percentage of tumor lymphocyte infiltrate in the Brain tumor explants of the SCID mice. The tumor explants were minced and using Percoll/Ficoll gradient in order to extract the lympgocyte infiltrates. Using Flow cytometry, Percentage of CD3+C45+D3+ subset were evaluated; T cells expressing then artificial D3 receptor were highly present in the tumor comparing to non-transduced control T cells.

Conclusion:

Transducing T cells with ALCAM minimal binding domain derived from CD6; either monomer or multimer with or without signaling; significantly enables crossing the endothelium barrier and eventually mediates better trafficking and homing. ALCAM-CD6 interaction is a novel platform useful to harness and enhance the delivery of adoptive T cells, for example, to a pathological site. Useful applications include but are not restricted to:

a) Cancer: improved delivery of CART cells, cytotoxic T cells, NK cells and NKT cells among other immune effectors.

b) Autoimmunity: improved delivery of Tregs and/or Th17 in EAE and in MS.

c) Stroke: delivery of PG, MSC, stem cells to enhance healing.

d) Infection: delivery of anti-infectious agents.

Example 2

Studies of the Homing Platform

Figures 27A, 27B:
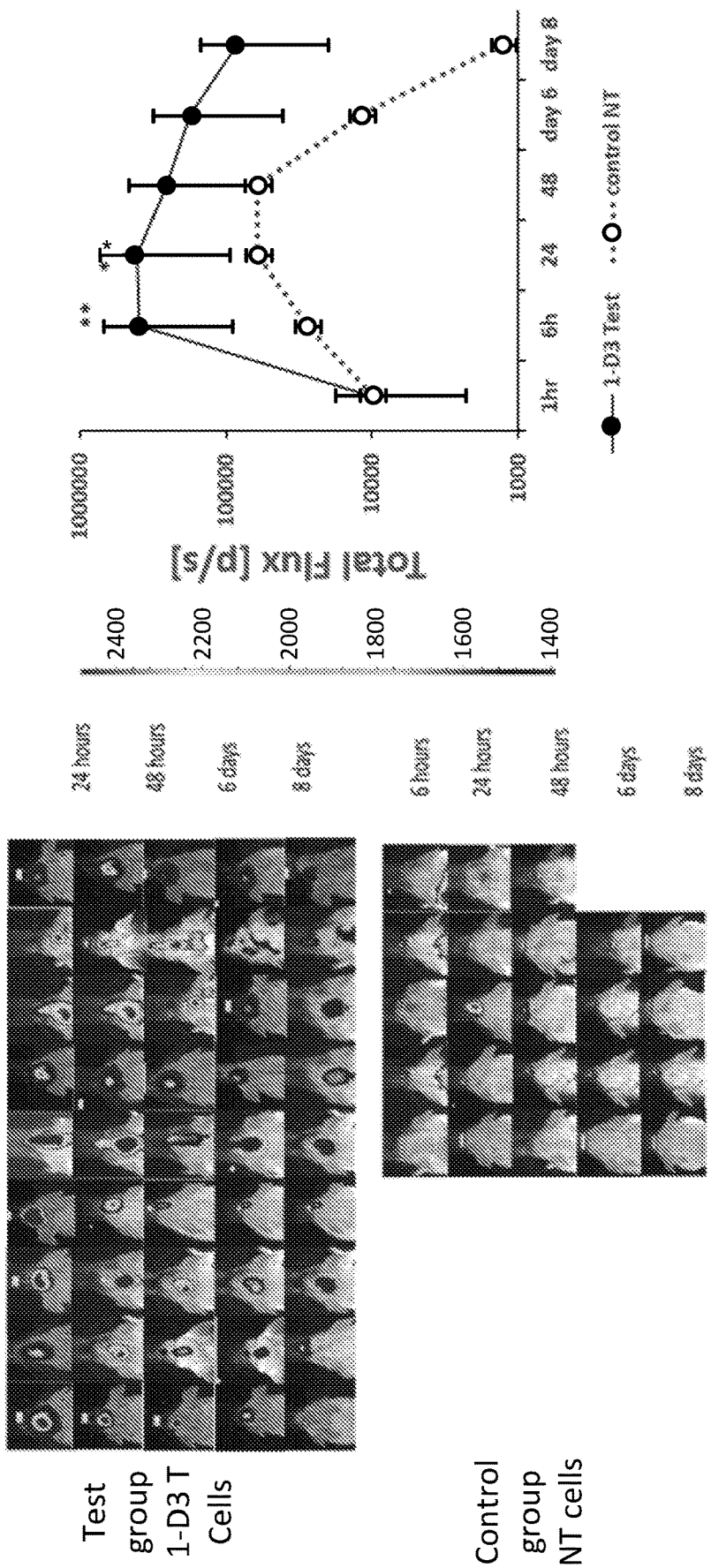
FIGS. 27A-27B show that D3 T-cells with full length CD6 signaling domain are effective in homing to brain in an orthotopic GBM model after IV infusion as assessed by optical Luceferin bioluminescence (BLI) tracking.
Figures 28A, 28B:
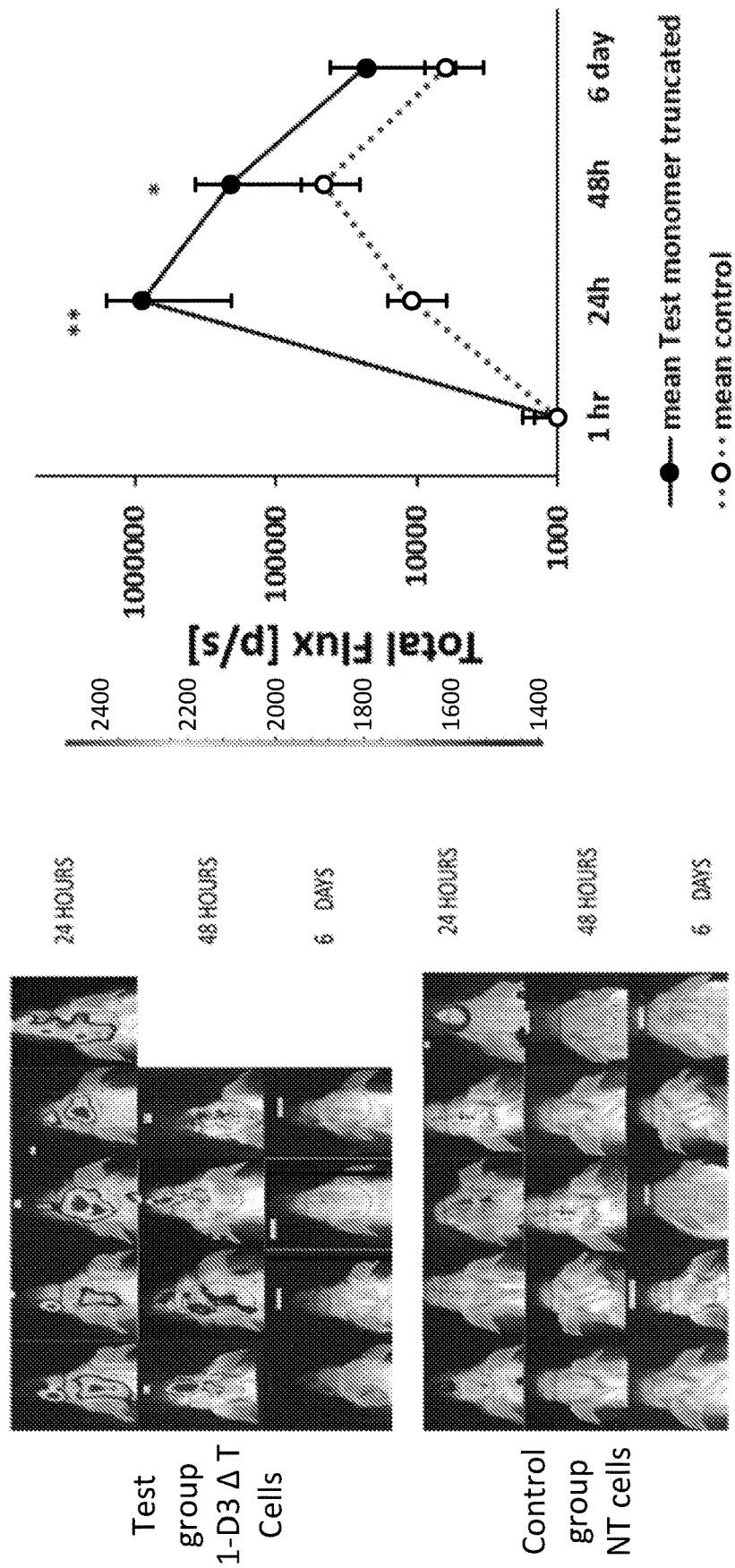
FIGS. 28A and 28B show D3 Δ-modified T-cells (the truncated D3 constructs) are effective in homing to a Brain orthotopic GBM model after IV infusion as assessed by optical luciferin bioluminescence (BLI) tracking.
Figure 30:
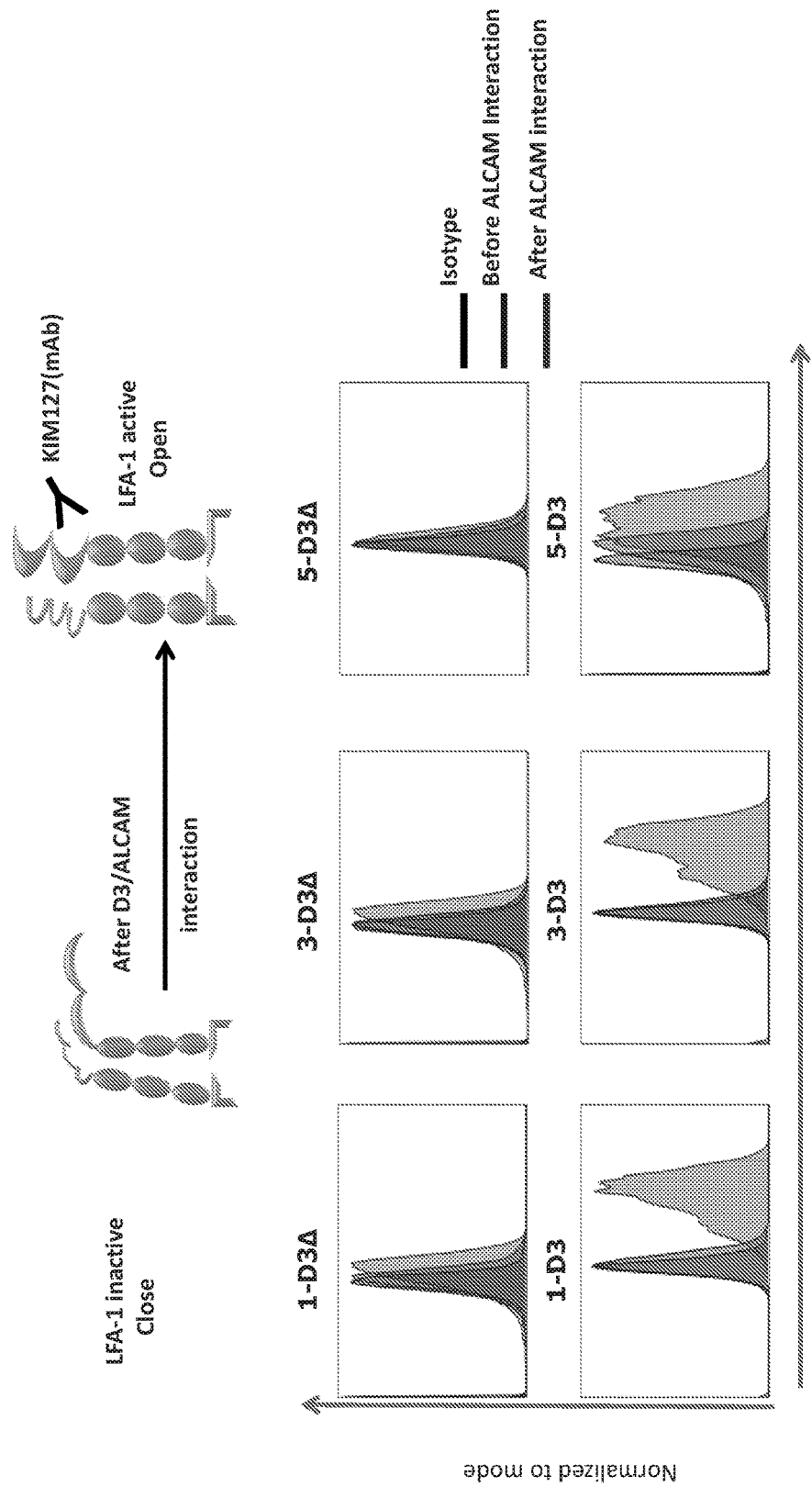
FIG. 30 shows D3 (MBE) successful induction of inside out activation of the LFA-1 (ubiquitous adhesion ligand over T cells mediating the efficient endothelial transmigration). LFA-1 extension or opening of the beta domain, is critical for high-affinity LFA-1, and it is detected by the reporter mAbs KIM127. T lymphocytes were fixed with 4% parafolmadehyde; then incubated with the biotin-labeled KIM127 mAbs (10 mg/ml) before and After ALCAM binding for one hours. Then The cells were then incubated with 2ndry antibody conjugated streptavidin labeled with Alexa Fluor 568-. Blue histogram denotes LFA-1 extended confirmation before ALCAM interaction and red histogram denotes LFA-1 open confirmation after ALCAM interaction A, respectively, and black lines denote background staining by a secondary only streptavidin Alexa-568.
Figure 31B:
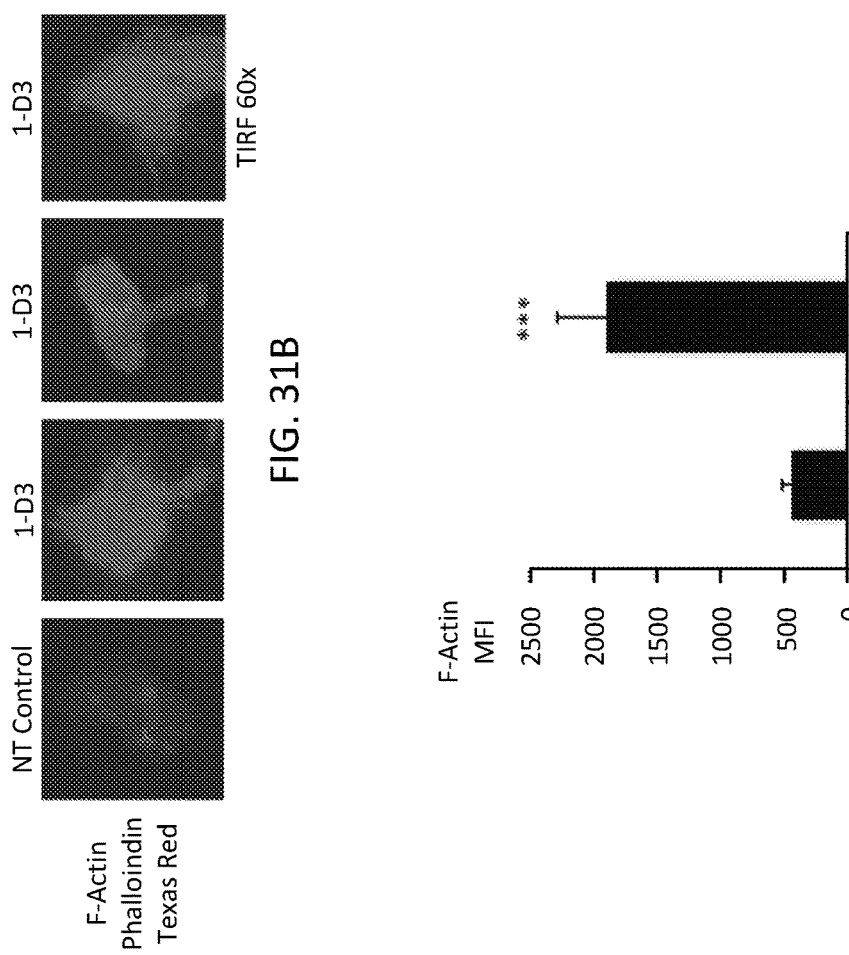
FIGS. 31A-31F.
Figure 31C:
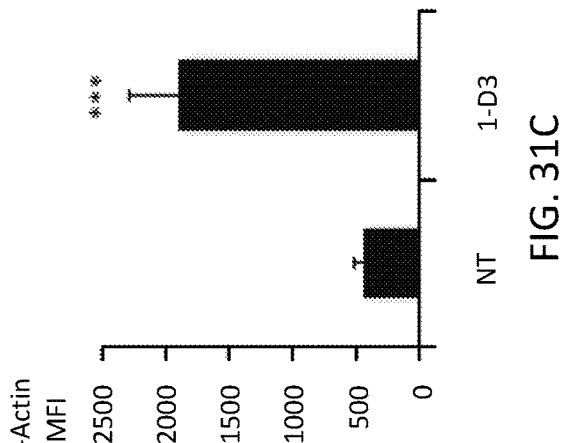
Figure 31A:
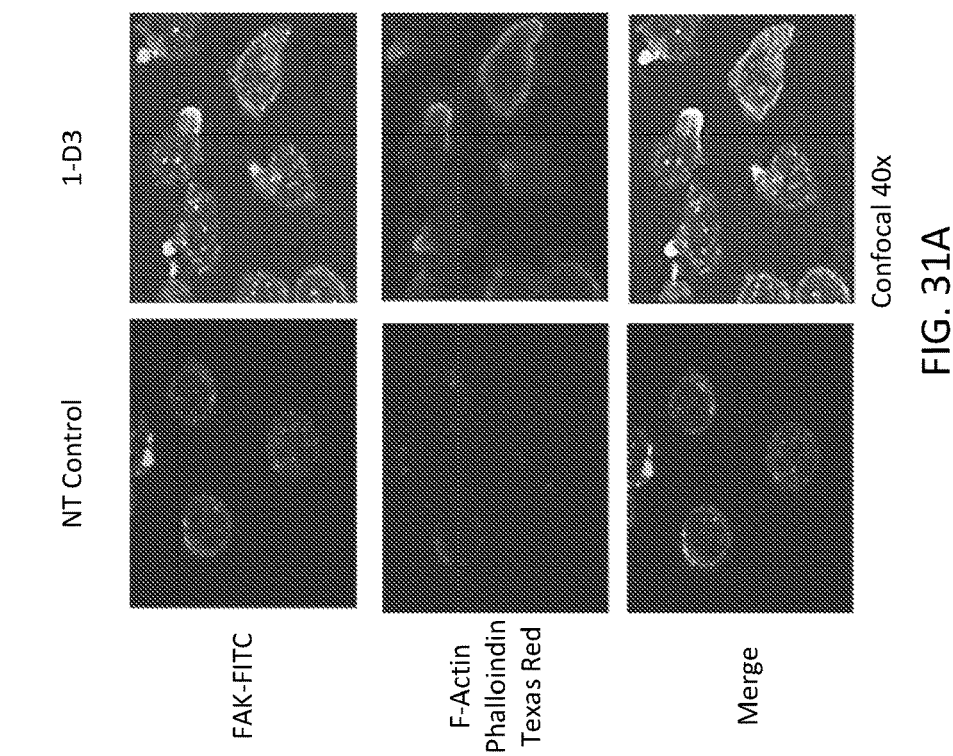
Figure 31D:
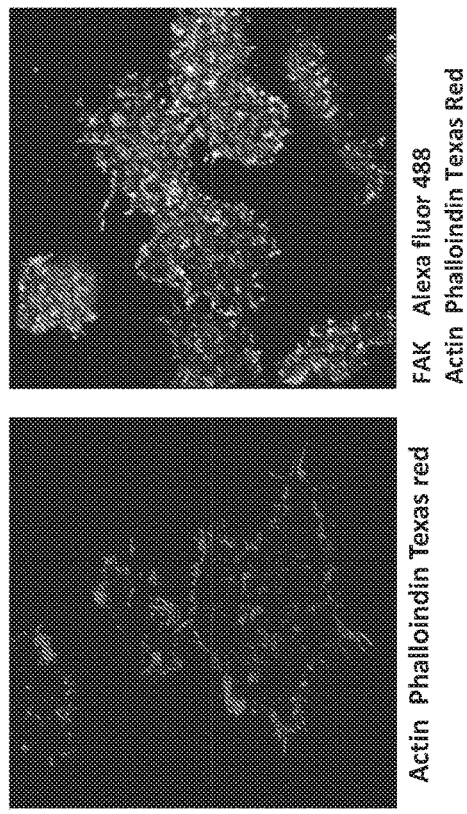
Figure 31E:
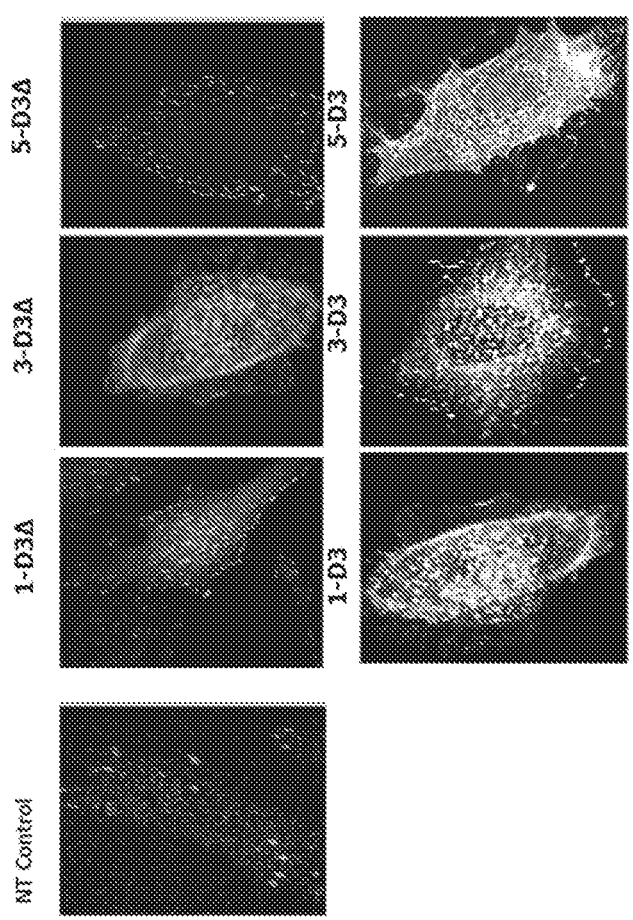
Figure 31F:
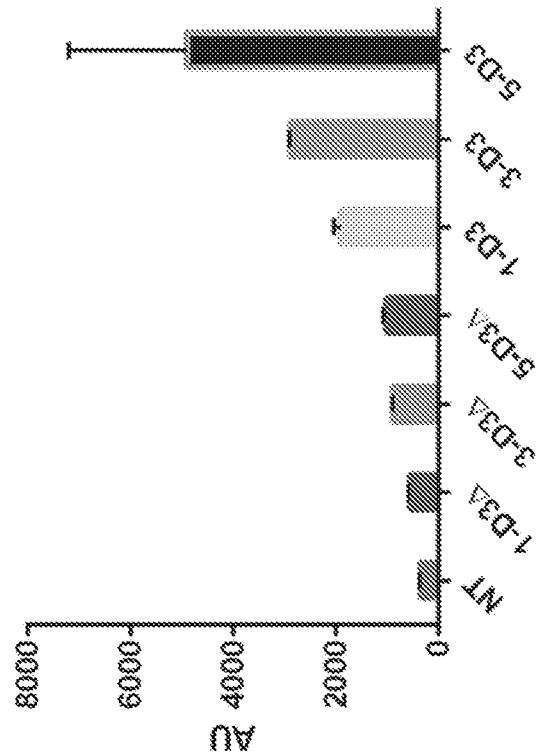

Embodiments of the platform were tested in an example of a GBM orthotopic model: the inventors utilized severe combined immune deficiency (SCID) mice of the NOD background that are homozygous for the spontaneous mutation Prkdcscid. Mice were injected intracranially with U87 GBM cell lines (50 k in 2-3 µl) on the right brain caudate using a stereotactic injector. Once tumors were established, T cells labeled with GFP ffluc were injected systemically through tail vein. The brain homing capacity was tracked using bioluminescent (BLI) imaging at different times on an IVIS Lumina platform under isoflurane anesthesia. Comparing a test group 1 that had CD6 D3-modified T cells to non-transduced (NT) control T cells, BLI signal in the brain at the tumor area were 2 fold higher than control NT (FIG. 27). These findings show that the CD6 D3 Platform successfully interacted with the ALCAM+BBB (induced by GBM tumor) that has allowed the efficient trafficking to tumor site. Moreover, T cells were injected IV and after 24 hrs, the mice were euthanized and the inventors isolated the Tumor infiltrating lymphocytes using Percoll/Ficoll gradient. Then, the inventors did a flow cytometry comparison between test (1-D3 T cells) and control (NT) where the flow cytometry was gated on for CD45+CD3+D3+ T cells in the brain tumor explants. There were highly significant D3 T cell infiltrates (***p<0.001) in tumor; almost 5 fold in comparison to NT control normal cells. Also truncated D3 Δ-modified T-cells (the truncated D3 constructs) are effective in homing but less persistent than D3 T cells with signaling Domains. IV infused D3 Δ-modified to a Brain orthotopic GBM model are evaluated in the same previously described method; by optical luceferin bioluminescence (BLI) tracking. FIG. 28A. Representative images of the in vivo bioluminescence imaging (BLI) of GFP ffluc+ T cell in the brain shown is the mean radiance (photons/second/cm$^2$/ selected region), where (n=10 per test group and n=5 per control). GBM orthotopic model were established in mice then at day 12, 10·10^6 T cells tagged with GFP ffluc IV were injected (n=10) either Test group 1-D3 Δ-modified T cells or control Non transduced (NT) group. Their luceferin BLI signals were detected in different time points after injection (6 hrs, 48 hrs, 6 days) FIG. 28B. Graph represents the fold change in the BLI of Test group 1-D3 in relation to control group. 1-D3Δ-modified (truncated) T cells have significant higher BLI in comparison with NT control T cells after 24 and 48 hrs; yet less than D3 T cells bearing the CD6 signaling domain. Data were analyzed by two-tailed student T test; Error bars are ±STEV; * P<0.05, P<0.01, *P<0.001.

FIGS. 29A, 29B, and 29C show [MBE]n_D3 T cell successful homing and infiltration in the tumor after 24 hrs IV administration. FIG. 29A. Flow cytometric comparison of D3 transduced T cells infiltrates gated in CD3+CD45+ subsets in the tumor explants vs. control NT cells. T cells were injected IV and after 24 hrs, the mice were euthanized and T cell infiltrates that were either D3 Test or NT were isolated using Percol/Ficoll and then stained with CD3-PerCP and CD45-APC and D3-PE for an hour. Analyses were done using Flowjo software. FIG. 29B. Graph represents percentage of human CD3 CD45 cells in GBM explants isolated from SCID mice. FIG. 29C. Percentage of CD6 D3+ transduced cells gated in the CD3+CD45+ subset. There is a high significance in D3 T cells homing to tumor and infiltration capacity compared to NT control T cells. Data were analyzed by 2-tailed Student T-test; Error bars are STEV; * P<0.05, P<0.01, *P<0.001. (n=5)

In one embodiment, one can improve the homing of regulatory T cells (Tregs) or the immune inhibitory Th17 to inflammatory conditions, such as multiple sclerosis and autoimmune encephalitis, graft versus host disease, rheumatoid disease and systemic lupus among others. One can establish an experimental autoimmune encephalomyelitis (EAE model, a model of brain inflammation) by subcutaneous injection in SJL mice with proteolipid protein (PLP), myelin basic protein (MBP), or peptides corresponding to the immunodominant epitopes of MBP (MBP84-104), MOG (MOG92-106), or PLP (PLP139-151 and PLP178-191). Then, one can infuse Tregs or Th17 cells modified with CD6 D3 molecules to improve their trafficking to MS or autoimmune lesions. The mice are monitored using the clinical score for 1 month. Then after a month mice are euthanized to assess differential inflammatory cells/Tregs ratio into the meninges and parenchyma of the spinal cord and brainstem, for example.

More globally one can use the [MBE]$^n$ CD6 D3 platform in broader preclinical investigation to improve the trafficking problem of any therapeutic modality that is the major cause of pharmacokinetic inefficacy and failure of the intended cure, such as in the CNS. CD6 D3 can be incorporated as adhesion molecule modulator on other cellular platforms, such as Natural killer cells for cancer immunotherapy, dendritic cells for vaccines delivery, red blood cells for drug delivery, stem cells for tissue regeneration, etc.

Furthermore, preclinically a [MBE]$^n$ CD6 D3 engineered molecule can be incorporated into cell membrane-camouflaged nanoparticles, microsomes, and/or dendrisomes. Additionally, the CD6 D3 molecule can be produced in a secreted form or as a preparation for priming ex vivo generated cells to enable them to target tissues with pathology such as cancer, inflammation, infection and so on. Thus, the [MBE]n CD6 D3 modular innovation is a useful delivery booster for breaching the endothelial/epithelial barrier, allowing better target penetration, such as in the BBB; in the context of ALCAM specificity. In addition of D3 platform as an adjunct for therapeutics modality, it can be used as delivery vehicle for Vaccines, anti-Cancer agent, anti-angiogenic as well as anti-thrombotic agent. Also, it can be gene editing delivery tool that specifically target ALCAM+ cells. Moreover, modulating the density of D3 (MBE) on a cell or biomimic agent can be a tactic for inducing ischemia. This extra potential is beneficial for the treatment of cancer, by cutting off blood supply; facilitating its subsequent residual removal. Also ischemia induction with [MBE]$^n$ CD6 D3 modular platform might help in easing transplantation surgeries. In particular embodiments, [MBE]$^n$ CD6 D3 on immune cells is a stabilizer for efficient immune synapse formation and is an agent for the intended activity. Alteration of D3 is useful in designing better therapeutic products based on adhesion affinity with ALCAM positive targets.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A therapeutic composition comprising
   a) at least one therapeutic moiety; said moiety operably linked to one or more of
   b) adhesion molecule binding moiety, wherein the adhesion molecule is ALCAM and the binding moiety is part or all of cluster of differentiation 6 (CD6).

2. The composition of claim 1, wherein the part or all of CD6 comprises at least one D3 region of the CD6 scavenger receptor cysteine rich domain and at least one CD6 stalk domain.

3. The composition of claim 2, wherein the part or all of CD6 comprises a secretable form of minimal binding element (MBE)n CD6 D3 or the multiplicity thereof.

4. The composition of claim 1, wherein the therapeutic moiety comprises a cell, small molecule, protein, peptide, nucleic acid, viral genome or coat, exosomes, dendrimers, biomimic nanoparticles, micelles, liposomes, or combination thereof.

5. The composition of claim 4, wherein the therapeutic moiety comprises a cell.

6. The composition of claim 5, wherein the cell is an immune cell, stem cell, mesenchymal stromal cell (MSC), or hybridoma.

7. The composition of claim 6, wherein the immune cell is a T cell, NK cell, NK T cell, B cell, Th17, dendritic cell, or T regulatory cell.

8. The composition of claim 6, wherein the stem cell is hematopoietic stem cell or mesenchymal stem cell.

9. A therapeutic composition comprising:
   a) at least one therapeutic moiety; said moiety operably linked to one or more of
   b) adhesion molecule binding moiety, wherein the adhesion molecule is ICAM-1 and the binding moiety for ICAM-1 comprises part or all of MAC-1 and/or part or all of LFA-1.

10. A therapeutic composition comprising:
    a) at least one therapeutic moiety; said moiety operably linked to one or more of
    b) adhesion molecule binding moiety, wherein the adhesion molecule is JAM-1 and the binding moiety for JAM-1 comprises part or all of MAC-1 and/or part or all of LFA-1.

11. The composition of claim 10, wherein the therapeutic moiety comprises a cell, small molecule, protein, peptide, nucleic acid, viral genome or coat, exosomes, dendrimers, biomimic nanoparticles, micelles, liposomes, or combination thereof.

12. The composition of claim 11, wherein the therapeutic moiety comprises a cell.

13. The composition of claim 12, wherein the cell is an immune cell, stem cell, mesenchymal stromal cell (MSC), or hybridoma.

14. The composition of claim 13, wherein the immune cell is a T cell, NK cell, NK T cell, B cell, Th17, dendritic cell, or T regulatory cell.

15. The composition of claim 13, wherein the stem cell is hematopoietic stem cell or mesenchymal stem cell.

16. A therapeutic composition comprising:
    a) at least one therapeutic moiety; said moiety operably linked to one or more of
    b) adhesion molecule binding moiety, wherein the adhesion molecule is GLYCAM-1 and the binding moiety for GLYCAM-1 comprises part or all of LPAM-1.

17. The composition of claim 16, wherein the therapeutic moiety comprises a cell, small molecule, protein, peptide, nucleic acid, viral genome or coat, exosomes, dendrimers, biomimic nanoparticles, micelles, liposomes, or combination thereof.

18. The composition of claim 17, wherein the therapeutic moiety comprises a cell.

19. The composition of claim 18, wherein the cell is an immune cell, stem cell, mesenchymal stromal cell (MSC), or hybridoma.

20. The composition of claim 19, wherein the immune cell is a T cell, NK cell, NK T cell, B cell, Th17, dendritic cell, or T regulatory cell.

21. The composition of claim 19, wherein the stem cell is hematopoietic stem cell or mesenchymal stem cell.

22. A therapeutic composition comprising:
    a) at least one therapeutic moiety; said moiety operably linked to one or more of
    b) adhesion molecule binding moiety, wherein the adhesion molecule is Addressin and the binding moiety for Addressin comprises part or all of LPAM-1.

23. The composition of claim 22, wherein the therapeutic moiety comprises a cell, small molecule, protein, peptide, nucleic acid, viral genome or coat, exosomes, dendrimers, biomimic nanoparticles, micelles, liposomes, or combination thereof.

24. The composition of claim 23, wherein the therapeutic moiety comprises a cell.

25. The composition of claim 24, wherein the cell is an immune cell, stem cell, mesenchymal stromal cell (MSC), or hybridoma.

26. The composition of claim 25, wherein the immune cell is a T cell, NK cell, NK T cell, B cell, Th17, dendritic cell, or T regulatory cell.

27. The composition of claim 25, wherein the stem cell is hematopoietic stem cell or mesenchymal stem cell.

* * * * *